United States Patent [19]

Kjeldsen et al.

[11] Patent Number: 5,639,642
[45] Date of Patent: Jun. 17, 1997

[54] SYNTHETIC LEADER PEPTIDE SEQUENCES

[75] Inventors: Thomas Børglum Kjeldsen, Kvædevej; Knud Vad, Frederiksberg, both of Denmark

[73] Assignee: Novo Nordisk A/S, Bagsvaerd, Denmark

[21] Appl. No.: 468,674

[22] Filed: Jun. 6, 1995

Related U.S. Application Data

[63] Continuation-in-part of Ser. No. 282,852, Jul. 29, 1994, abandoned.

[30] Foreign Application Priority Data

Jun. 16, 1994 [DK] Denmark ................................. 0705/94

[51] Int. Cl.$^6$ .......................... C02D 21/00; C12N 15/00; C07H 21/04
[52] U.S. Cl. .................. 435/697; 435/172.1; 536/23.4; 536/23.5; 536/24.1
[58] Field of Search ............................... 435/69.7, 172.1; 536/23.5, 23.4, 24.1

[56] References Cited

U.S. PATENT DOCUMENTS 5,037,743 8/1991 Welch et al. ............................. 435/69.1

FOREIGN PATENT DOCUMENTS 0 324 274 7/1989 European Pat. Off. .
WO 92/11378 7/1992 WIPO .

*Primary Examiner*—James Ketter
*Assistant Examiner*—John S. Brusca
*Attorney, Agent, or Firm*—Steve T. Zelson, Esq.; Elias J. Lambiris, Esq.

[57] ABSTRACT

The present invention relates to a DNA expression cassette comprising the following sequence:

5'-P-SP-LS-PS-*gene*-(T)$_i$-3' wherein

P is a promoter sequence,

SP is a DNA sequence encoding a signal peptide,

LS is a DNA sequence encoding a leader peptide of formula I:

GlnProIle(Asp/Glu)(Asp/Glu)X$^1$(Glu/Asp)X$^2$AsnZ(Thr/Ser)X$^3$ (SEQ ID NO: 77) (I)

wherein

X$^1$ is a peptide bond or a codable amino acid;

X$^2$ is a peptide bond, a codable amino acid or a sequence of up to 4 codable amino acids which may be the same or different;

Z is a codable amino acid except Pro; and

X$^3$ is a sequence of from 4 to 30 codable amino acids which may be the same or different;

PS is a DNA sequence encoding a processing site;

*gene* is a DNA sequence encoding a polypeptide;

T is a terminator sequence; and i is 0 or 1.

17 Claims, 9 Drawing Sheets

Fig. 2

EcoR I

GAATTCATTCAAGAATAGT

CTTAAGTAAGTTCTTATCA

TCAAACAAGAAGATTACAAACTATCAATTTCATACACAATATAAACGACGGGTACCAAAA
AGTTTGTTCTTCTAATGTTTGATAGTTAAAGTATGTGTTATATTTGCTGCCCATGGTTTT

TAATGAAACTGAAAACTGTAAGATCTGCGGTCCTTTCGTCACTCTTTGCATCTCAGGTCC
ATTACTTTGACTTTTGACATTCTAGACGCCAGGAAAGCAGTGAGAAACGTAGAGTCCAGG
    M  K  L  K  T  V  R  S  A  V  L  S  S  L  F  A  S  Q  V  L

TTGGCCAACCAATAGACGAAGACAACGACACTTCTTCCATGGCTAAGAGATTCGTTAACC
AACCGGTTGGTTATCTGCTTCTGTTGCTGTGAAGAAGGTACCGATTCTCTAAGCAATTGG
    G  Q  P  I  D  E  D  N  D  T  S  S  M  A  K  R  F  V  N  Q

AACACTTGTGCGGTTCCCACTTGGTTGAAGCTTTGTACTTGGTTTGCGGTGAAAGAGGTT
TTGTGAACACGCCAAGGGTGAACCAACTTCGAAACATGAACCAAACGCCACTTTCTCCAA
    H  L  C  G  S  H  L  V  E  A  L  Y  L  V  C  G  E  R  G  F

TCTTCTACACTCCTAAGGCTGCTAAGGGTATTGTCGAGCAATGCTGTACCTCCATCTGCT
AGAAGATGTGAGGATTCCGACGATTCCCATAACAGCTCGTTACGACATGGAGGTAGACGA
    F  Y  T  P  K  A  A  K  G  I  V  E  Q  C  C  T  S  I  C  S

Xba I
CCTTGTACCAATTGGAAAACTACTGCAACTAGACGCAGCCCGCAGGCTCTAGA    SEQ   ID
No.40
GGAACATGGTTAACCTTTTGATGACGTTGATCTGCGTCGGGCGTCCGAGATCT
   L  Y  Q  L  E  N  Y  C  N  *                      SEQ ID
No.41

Fig. 3
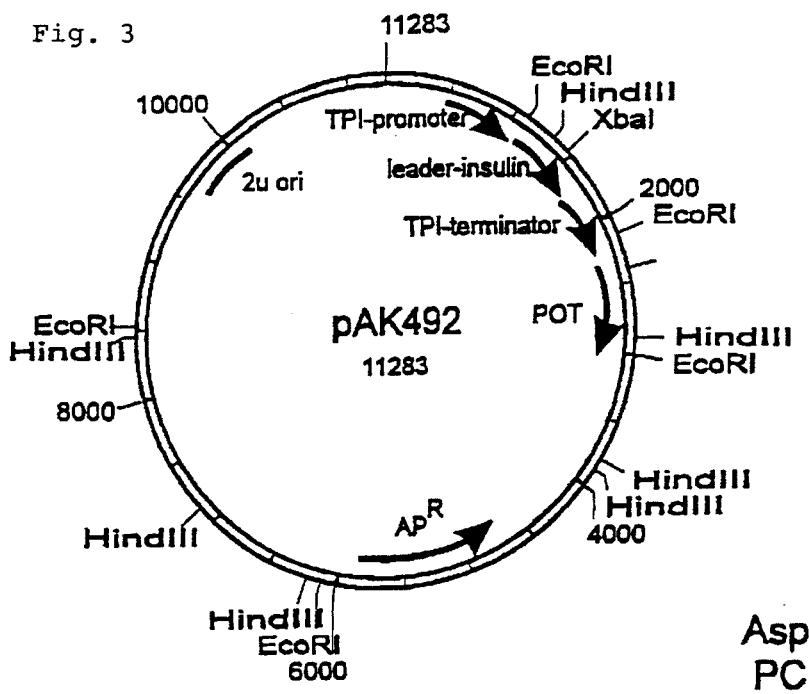
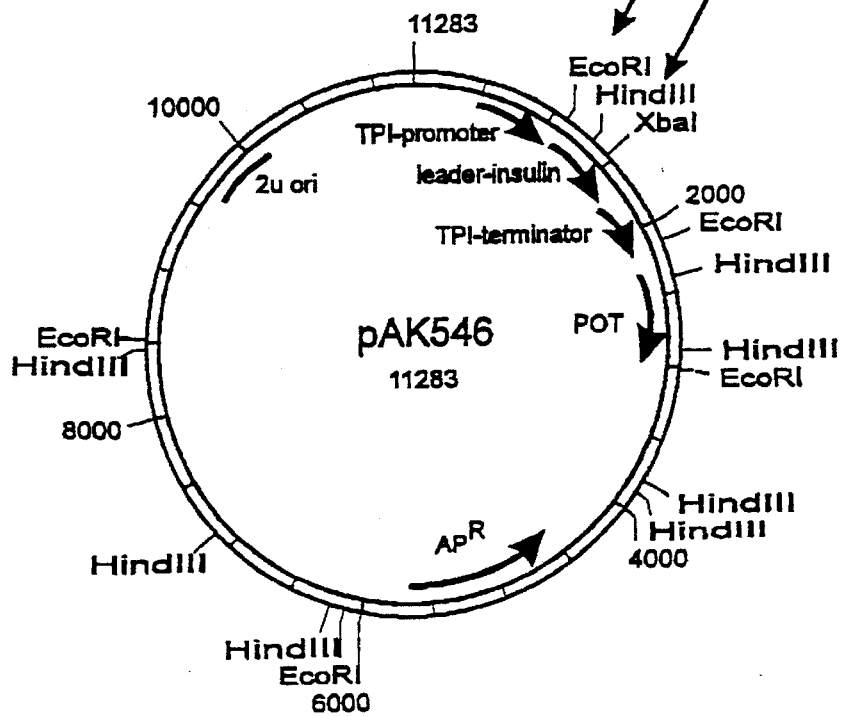

Fig. 4.
CAACCAATTGACGACGAAAACACTACTTCTGTCAACTTGCCAGTT  SEQ ID No. 42
GTTGGTTAACTGCTGCTTTTGTGATGAAGACAGTTGAACGGTCAA
GlnProIleAspAspGluAsnThrThrSerValAsnLeuProVal  SEQ ID No. 43

Fig. 5.
ATGAAACTGAAAACTGTAAGATCTGCGGTCCTTTCGTCACTCTTTGCA
TACTTTGACTTTTGACATTCTAGACGCCAGGAAAGCAGTGAGAAACGT
MetLysLeuLysThrValArgSerAlaValLeuSerSerLeuPheAla

TCTCAGGTCCTTGGCCAACCAATTGACGACGAAAACACTACTTCTGTC
AGAGTCCAGGAACCGGTTGGTTAACTGCTGCTTTTGTGATGAAGACAG
SerGlnValLeuGlyGlnProIleAspAspGluAsnThrThrSerVal

AACTTGCCAGTTAAGAGATTCGTTAACCAACACTTGTGTGGTTCTCAC
TTGAACGGTCAATTCTCTAAGCAATTGGTTGTGAACACACCAAGAGTG
AsnLeuProValLysArgPheValAsnGlnHisLeuCysGlySerHis

TTGGTTGAAGCTTTGTACTTGGTTTGCGGTGAAAGAGGTTTCTTCTAC
AACCAACTTCGAAACATGAACCAAACGCCACTTTCTCCAAAGAAGATG
LeuValGluAlaLysTyrLeuValCysGlyGluArgGlyPhePheTyr

ACTCCTAAGGCTGCTAAGGGTATTGTCGAACAATGCTGTACCTCCATC
TGAGGATTCCGACGATTCCCATAACAGCTTGTTACGACATGGAGGTAG
TyrProLysAlaAlaLysGlyIleValGluGlnCysCysThrSerIle

TGCTCCTTGTACCAATTGGAAAACTACTGCAACTAGACGCAGCCCGCA
ACGAGGAACATGGTTAACCTTTTGATGACGTTGATCTGCGTCGGGCGT
CysSerLeuTyrGlnLeuGluAsnTyrCysAsn*  SEQ ID No. 45

GGCTCTAGA  SEQ ID No. 44
CCGAGATCT

Fig. 6.
CAACCAATTGACGACACTGAATCTAACACTACTTCTGTCAACTTGCCAGCT SEQ ID No. 46
GTTGGTTAACTGCTGTGACTTAGATTGTGATGAAGACAGTTGAACGGTCGA
GlnProIleAspAspThrGluSerAsnThrThrSerValAsnLeuProAla SEQ ID No. 47

Fig. 7.
CAACCAATTGACGACACTGAATCTAACACTACTTCTGTCAACTTGCCA
GTTGGTTAACTGCTGTGACTTAGATTGTGATGAAGACAGTTGAACGGT
GlnProIleAspAspThrGluSerAsnThrThrSerValAsnLeuPro

GGTGCT  SEQ ID No. 48
CCACGA
GlyAla  SEQ ID No. 8

Fig. 8.
CAACCAATTGACGACACTGAATCTATCAACACTACTTTGGTCAACTTG
GTTGGTTAACTGCTGTGACTTAGATAGTTGTGATGAAACCAGTTGAAC
GlnProIleAspAspThrGluSerIleAsnThrThrLeuValAsnLeu

CCAGGTGCT  SEQ ID No. 49
GGTCCACGA
ProGlyAla  SEQ ID No. 17

Fig. 9.
CAACCAATTGACGACACTGAATCTAACACTACTTCTGTCAACTTGATG
GTTGGTTAACTGCTGTGACTTAGATTGTGATGAAGACAGTTGAACTAC
GlnProIleAspAspThrGluSerAsnThrThrSerValAsnLeuMet

GCTGACGACACTGAATCTATCAACACTACTTTGGTTAACTTGCCAGGTGCT   SEQ ID No. 50
CGACTGCTGTGACTTAGATAGTTGTGATGAAACCAATTGAACGGTCCACGA
AlaAspAspThrGluSerIleAsnThrThrLeuValAsnLeuProGlyAla   SEQ ID No. 16

Fig. 10.
CAACCAATTGACGACACTGAATCTAACACTACTTCTGTCAACTTGATGGCTGACGACACT
GTTGGTTAACTGCTGTGACTTAGATTGTGATGAAGACAGTTGAACTACCGACTGCTGTGA
GlnProIleAspAspThrGluSerAsnThrThrSerValAsnLeuMetAlaAspAspThr

GAATCTAGATTCGCTACTAACACTACTTTGGTTAACTTGCCATTG         SEQ ID No. 51
CTTAGATCTAAGCGATGATTGTGATGAAACCAATTGAACGGTAAC
GluSerArgProAlaThrAsnThrThrLeuValAsnLeuProLeu         SEQ ID No. 19

Fig. 11
CAACCAATTGACGACACTGAATCTAACACTACTTCTGTCAACTTGATGGCTGACGACACT
GTTGGTTAACTGCTGTGACTTAGATTGTGATGAAGACAGTTGAACTACCGACTGCTGTGA
GlnProIleAspAspThrGluSerAsnThrThrSerValAsnLeuMetAlaAspAspThr

GAATCTATCAACACTACTTTGGTTAACTTGGCTAACGTTGCCATGGCT      SEQ ID No. 52
CTTAGATAGTTGTGATGAAACCAATTGAACCGATTGCAACGGTACCGA
GluSerIleAsnThrThrLeuValAsnLeuAlaAsnValAlaMetAla      SEQ ID No. 20

Fig. 12.
CAACCAATTGACGACACTGAATCTGCTATCAACACTACTTTGGTCAAC
GTTGGTTAACTGCTGTGACTTAGACGATAGTTGTGATGAAACCAGTTG
GlnProIleAspAspThrGluSerAlaIleAsnThrThrLeuValAsn

TTGCCAGGTGCT                                          SEQ ID No. 53
AACGGTCCACGA
LeuProGlyAla                                          SEQ ID No. 21

Fig. 13
pAK527:
   TTAAATCTATAACTACAAAAAACACATACAGGAATTCATTCAAGAATAGTTCAAACAA
   AATTTAGATATTGATGTTTTTTGTGTATGTCCTTAAGTAAGTTCTTATCAAGTTTGTT

GAAGATTACAAACTATCAATTTCATACACAATATAAACGACGGGTACCAAAATAATGAAA
CTTCTAATGTTTGATAGTTAAAGTATGTGTTATATTTGCTGCCCATGGTTTTATTACTTT
                                                          MetLys

CTGAAAACTGTAAGATCTGCGGTCCTTTCGTCACTCTTTGCATCTCAGGTCCTTGGCCAA
GACTTTTGACATTCTAGACGCCAGGAAAGCAGTGAGAAACGTAGAGTCCAGGAACCGGTT
LeuLysThrValArgSerAlaValLeuSerSerLeuPheAlaSerGlnValLeuGlyGln

CCAATTGACGACGAAAACACTACTTCTGTTAACTTGCCAGCTAAGAGATTCGTTAACCAA
GGTTAACTGCTGCTTTTGTGATGAAGACAATTGAACGGTCGATTCTCTAAGCAATTGGTT
ProIleAspAspGluAsnThrThrSerValAsnLeuProAlaLysArgPheValAsnGln

CACTTGTGCGGTTCCCACTTGGTTGAAGCTTTGTACTT                SEQ ID No. 54
GTGAACACGCCAAGGGTGAACCAACTTCGAAACATGAA
HisLeuCysGlySerHisLeuValGluAlaLeuTyr                  SEQ ID No. 55

Fig. 14 pAK531:
```
   TTAAATCTATAACTACAAAAAACACATACAGGAATTCATTCAAGAATAGTTCAAACAA
   AATTTAGATATTGATGTTTTTTGTGTATGTCCTTAAGTAAGTTCTTATCAAGTTTGTT

GAAGATTACAAACTATCAATTTCATACACAATATAAACGACGGGTACCAAAATAATGAAA
CTTCTAATGTTTGATAGTTAAAGTATGTGTTATATTTGCTGCCCATGGTTTTATTACTTT
                                                         MetLys

CTGAAAACTGTAAGATCTGCGGTCCTTTCGTCACTCTTTGCATCTCAGGTCCTTGGCCAA
GACTTTTGACATTCTAGACGCCAGGAAAGCAGTGAGAAACGTAGAGTCCAGGAACCGGTT
LeuLysThrValArgSerAlaValLeuSerSerLeuPheAlaSerGlnValLeuGlyGln

CCAATTGACGACACTGAATCTAACACTACTTCTGTCAACTTGCCAGCTAAGAGATTCGTT
GGTTAACTGCTGTGACTTAGATTGTGATGAAGACAGTTGAACGGTCGATTCTCTAAGCAA
ProIleAspAspThrGluSerAsnThrThrSerValAsnLeuProAlaLysArgPheVal

AACCAACACTTGTGCGGTTCCCACTTGGTTGAAGCTTTGTACTT           SEQ ID No. 56
TTGGTTGTGAACACGCCAAGGGTGAACCAACTTCGAAACATGAA
AsnGlnHisLeuCysGlySerHisLeuValGluAlaLeuTyr            SEQ ID No. 57
```

Fig. 15 pAK555
```
   TTAAATCTATAACTACAAAAAACACATACAGGAATTCATTCAAGAATAGTTCAAACAA
   AATTTAGATATTGATGTTTTTTGTGTATGTCCTTAAGTAAGTTCTTATCAAGTTTGTT

GAAGATTACAAACTATCAATTTCATACACAATATAAACGACGGGTACCAAAATAATGAAA
CTTCTAATGTTTGATAGTTAAAGTATGTGTTATATTTGCTGCCCATGGTTTTATTACTTT
                                                         MetLys

CTGAAAACTGTAAGATCTGCGGTCCTTTCGTCACTCTTTGCATCTCAGGTCCTTGGCCAA
GACTTTTGACATTCTAGACGCCAGGAAAGCAGTGAGAAACGTAGAGTCCAGGAACCGGTT
LeuLysThrValArgSerAlaValLeuSerSerLeuPheAlaSerGlnValLeuGlyGln

CCAATTGACGACACTGAATCTAACACTACTTCTGTCAACTTGATGGCTAAGAGATTCGTT
GGTTAACTGCTGTGACTTAGATTGTGATGAAGACAGTTGAACTACCGATTCTCTAAGCAA
ProIleAspAspThrGluSerAsnThrThrSerValAsnLeuMetAlaLysArgPheVal

AACCAACACTTGTGCGGTTCCCACTTGGTTGAAGCTTTGTACTT           SEQ ID No. 58
TTGGTTGTGAACACGCCAAGGGTGAACCAACTTCGAAACATGAA
AsnGlnHisLeuCysGlySerHisLeuValGluAlaLeuTyr            SEQ ID No. 59
```

Fig. 16 pAK559:
```
   TTAAATCTATAACTACAAAAAACACATACAGGAATTCATTCAAGAATAGTTCAAACAA
   AATTTAGATATTGATGTTTTTTGTGTATGTCCTTAAGTAAGTTCTTATCAAGTTTGTT

GAAGATTACAAACTATCAATTTCATACACAATATAAACGACGGGTACCAAAATAATGAAA
CTTCTAATGTTTGATAGTTAAAGTATGTGTTATATTTGCTGCCCATGGTTTTATTACTTT
                                                         MetLys

CTGAAAACTGTAAGATCTGCGGTCCTTTCGTCACTCTTTGCATCTCAGGTCCTTGGCCAA
GACTTTTGACATTCTAGACGCCAGGAAAGCAGTGAGAAACGTAGAGTCCAGGAACCGGTT
LeuLysThrValArgSerAlaValLeuSerSerLeuPheAlaSerGlnValLeuGlyGln

CCAATTGACGACACTGAATCTAACACTACTTCTGTCAACTTGATGGCTGACGACACTGAA
GGTTAACTGCTGTGACTTAGATTGTGATGAAGACAGTTGAACTACCGACTGCTGTGACTT
ProIleAspAspThrGluSerAsnThrThrSerValAsnLeuMetAlaAspAspThrGlu
```

```
TCTATCAACACTACTTTGGTTAACTTGCCAGGTGCTAAGAGATTCGTTAACCAACACTTG
AGATAGTTGTGATGAAACCAATTGAACGGTCCACGATTCTCTAAGCAATTGGTTGTGAAC
SerIleAsnThrThrLeuValAsnLeuProGlyAlaLysArgPheValAsnGlnHisLeu

TGCGGTTCCCACTTGGTTGAAGCTTTGTACTT                    SEQ ID No. 60
ACGCCAAGGGTGAACCAACTTCGAAACATGAA
CysGlySerHisLeuValGluAlaLeuTyr                      SEQ ID No. 61
```

Fig. 17
pAK562:
```
   TTAAATCTATAACTACAAAAAACACATACAGGAATTCATTCAAGAATAGTTCAAACAA
   AATTTAGATATTGATGTTTTTTGTGTATGTCCTTAAGTAAGTTCTTATCAAGTTTGTT

GAAGATTACAAACTATCAATTTCATACACAATATAAACGACGGGTACCAAAATAATGAAA
CTTCTAATGTTTGATAGTTAAAGTATGTGTTATATTTGCTGCCCATGGTTTTATTACTTT
                                                        MetLys

CTGAAAACTGTAAGATCTGCGGTCCTTTCGTCACTCTTTGCATCTCAGGTCCTTGGCCAA
GACTTTTGACATTCTAGACGCCAGGAAAGCAGTGAGAAACGTAGAGTCCAGGAACCGGTT
LeuLysThrValArgSerAlaValLeuSerSerLeuPheAlaSerGlnValLeuGlyGln

CCAATTGACGACACTGAATCTATCAACACTACTTTGGTCAACTTGCCAGGTGCTAAGAGA
GGTTAACTGCTGTGACTTAGATAGTTGTGATGAAACCAGTTGAACGGTCCACGATTCTCT
ProIleAspAspThrGluSerIleAsnThrThrLeuValAsnLeuProGlyAlaLysArg

TTCGTTAACCAACACTTGTGCGGTTCCCACTTGGTTGAAGCTTTGTACTT  SEQ ID No. 62
AAGCAATTGGTTGTGAACACGCCAAGGGTGAACCAACTTCGAAACATGAA
PheValAsnGlnHisLeuCysGlySerHisLeuValGluAlaLeuTyr    SEQ ID No. 63
```

Fig. 18
```
CAACCAATTGACGACACTGAATCTAACACTACTTCTGTCAACTTGATG
GTTGGTTAACTGCTGTGACTTAGATTGTGATGAAGACAGTTGAACTAC
GlnProIleAspAspThrGluSerAsnThrThrSerValAsnLeuMet

GCTGACGACACTGAATCTAGATTCGCTACTAACACTACTTTGGATGTT
CGACTGCTGTGACTTAGATCTAAGCGATGATTGTGATGAAACCTACAA
AlaAspAspThrGluSerArgPheAlaThrAsnThrThrLeuAspVal

GTTAACTTGATCTCCATGGCT                SEQ ID No. 66
CAATTGAACTAGAGGTACCGA
ValAsnLeuIleSerMetAla                SEQ ID No. 27
```

Fig. 19
```
AAGAGAGAAGAAGCTGAAGCTGAAGCTGAACCAAAGTTCGTTAACCAA
TTCTCTCTTCTTCGACTTCGACTTCGACTTGGTTTCAAGCAATTGGTT
LysArgGluGluAlaGluAlaGluAlaGluProLysPheValAsnGln

CACTTGTGTGGTTCTCACTTGGTTGAAGCTTTGTACTTGGTTTGCGGT
GTGAACACACCAAGAGTGAACCAACTTCGAAACATGAACCAAACGCCA
HisLeuCysGlySerHisLeuValGluAlaLeuTyrLeuValCysGly

GAAAGAGGTTTCTTCTACACTCCTAAGGCTGCTAAGGGTATTGTCGAA
CTTTCTCCAAAGAAGATGTGAGGATTCCGACGATTCCCATAACAGCTT
GluArgGlyPhePheTyrThrProLysAlaAlaLysGlyIleValGlu

CAATGCTGTACCTCCATCTGCTCCTTGTACCAATTGGAAAACTACTGC
GTTACGACATGGAGGTAGACGAGGAACATGGTTAACCTTTTGATGACG
GlnCysCysThrSerIleCysSerLeuTyrGlnLeuGluAsnTyrCys
```

```
                                        Xba I
AACTAGACGCAGCCCGCAGGCTCTAGA                              SEQ ID No. 70
TTGATCTGCGTCGGGCGTCCGAGATCT
Asn***                                                   SEQ ID No. 71
```

Fig. 20
```
CAACCAATTGACGACACTGAATCTAACACTACTTCTGTCAACTTGATG
GTTGGTTAACTGCTGTGACTTAGATTGTGATGAAGACAGTTGAACTAC
GlnProIleAspAspThrGluSerAsnThrThrSerValAsnLeuMet

GCTGACGACACTGAATCTAGATTCGCTACTAACACTACTTTGGCTTTG
CGACTGCTGTGACTTAGATCTAAGCGATGATTGTGATGAAACCGAAAC
AlaAspAspThrGluSerArgPheAlaThrAsnThrThrLeuAlaLeu
```
```
GATGTTGTTAACTTGATCTCCATGGCT                             SEQ ID No. 68
CTACAACAATTGAACTAGAGGTACCGA
AspValValAsnLeuIleSerMetAla                             SEQ ID No. 69
```

Fig. 21
pAK614
```
    TTAAATCTATAACTACAAAAAACACATACAGGAATTCCATTCAAGA
    AATTTAGATATTGATGTTTTTTGTGTATGTCCTTAAGGTAAGTTCT

ATAGTTCAAACAAGAAGATTACAAACTATCAATTTCATACACAATATA
TATCAAGTTTGTTCTTCTAATGTTTGATAGTTAAAGTATGTGTTATAT

AACGACGGTACCAAAATAATGAAACTGAAAACTGTAAGATCTGCGGTC
TTGCTGCCATGGTTTTATTACTTTGACTTTTGACATTCTAGACGCCAG
                       MetLysLeuLysThrValArgSerAlaVal

CTTTCGTCACTCTTTGCATCTCAGGTCCTTGGCCAACCAATTGACGAC
GAAAGCAGTGAGAAACGTAGAGTCCAGGAACCGGTTGGTTAACTGCTG
LeuSerSerLeuPheAlaSerGlnValLeuGlyGlnProIleAspAsp

ACTGAATCTAACACTACTTCTGTCAACTTGATGGCTGACGACACTGAA
TGACTTAGATTGTGATGAAGACAGTTGAACTACCGACTGCTGTGACTT
ThrGluSerAsnThrThrSerValAsnLeuMetAlaAspAspThrGlu

TCTAGATTCGCTACTAACACTACTTTGGTTAACTTGGCTAACGTTGCC
AGATCTAAGCGATGATTGTGATGAAACCAATTGAACCGATTGCAACGG
SerArgPheAlaThrAsnThrThrLeuValAsnLeuAlaAsnValAla

AACCAACACTTGTGTGGTTCTCACTTGGTTGAAGCTTTGTACTTATGG
TACCGATTCTCTAAGCAATTGGTTGTGAACACACCAAGAGTGAACCAA
MetAlaLysArgPheValAsnGlnHisLeuCysGlySerHisLeuVal
```
```
CTAAGAGATTCGTT                                          SEQ ID No. 72
CTTCGAAACATGAA                                          SEQ ID NO.73
GluAlaLeuTyr
```

Fig. 22
pAK625
```
    TTAAATCTATAACTACAAAAAACACATACAGGAATTCCATTCAAGA
    AATTTAGATATTGATGTTTTTTGTGTATGTCCTTAAGGTAAGTTCT

ATAGTTCAAACAAGAAGATTACAAACTATCAATTTCATACACAATATA
TATCAAGTTTGTTCTTCTAATGTTTGATAGTTAAAGTATGTGTTATAT
```

AACGACGGTACCAAAATAATGAAACTGAAAACTGTAAGATCTGCGGTC
TTGCTGCCATGGTTTTATTACTTTGACTTTTGACATTCTAGACGCCAG
                        MetLysLeuLysThrValArgSerAlaVal

CTTTCGTCACTCTTTGCATCTCAGGTCCTTGGCCAACCAATTGACGAC
GAAAGCAGTGAGAAACGTAGAGTCCAGGAACCGGTTGGTTAACTGCTG
LeuSerSerLeuPheAlaSerGlnValLeuGlyGlnProIleAspAsp

ACTGAATCTAACACTACTTCTGTCAACTTGATGGCTGACGACACTGAA
TGACTTAGATTGTGATGAAGACAGTTGAACTACCGACTGCTGTGACTT
ThrGluSerAsnThrThrSerValAsnLeuMetAlaAspAspThrGlu

TCTAGATTCGCTACTAACACTACTTTGGATGTTGTTAACTTGATCTCC
AGATCTAAGCGATGATTGTGATGAAACCTACAACAATTGAACTAGAGG
SerArgPheAlaThrAsnThrThrLeuAspValValAsnLeuIleSer

ATGGCTAAGAGAGAAGAAGCTGAAGCTGAAGCTGAACCAAAGTTCGTT
TACCGATTCTCTCTTCTTCGACTTCGACTTCGACTTGGTTTCAAGCAA
MetAlaLysArgGluGluAlaGluAlaGluAlaGluProLysPheVal

AACCAACACTTGTGTGGTTCTCACTTGGTTGAAGCTTTGTACTTG          SEQ ID No. 74
TTGGTTGTGAACACACCAAGAGTGAACCAACTTCGAAACATGAAC
AsnGlnHisLeuCysGlySerHisLeuValGluAlaLeuTyr            SEQ ID No. 75

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gln Pro Ile Asp Glu Asp Asn Asp Thr Ser Val Asn Leu Pro Ala
 1           5                  10                      15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gln Pro Ile Asp Asp Glu Asn Thr Thr Ser Val Asn Leu Pro Ala
 1           5                  10                      15
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gln Pro Ile Asp Asp Glu Ser Asn Thr Thr Ser Val Asn Leu Pro Ala
 1           5                  10                      15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gln Pro Ile Asp Asp Glu Asn Thr Thr Ser Val Asn Leu Pro Val
1               5                       10                      15

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Gln Pro Ile Asp Asp Thr Glu Asn Thr Thr Ser Val Asn Leu Pro Ala
1               5                       10                      15

( 2 ) INFORMATION FOR SEQ ID NO:6:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Gln Pro Ile Asp Asp Thr Glu Ser Asn Thr Thr Ser Val Asn Leu Pro
1               5                       10                      15
Ala ( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Gln Pro Ile Asp Asp Glu Asn Thr Thr Ser Val Asn Leu Met Ala
1               5                       10                      15

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Gln Pro Ile Asp Asp Thr Glu Ser Asn Thr Thr Ser Val Asn Leu Pro
1               5                       10                      15
Gly Ala ( 2 ) INFORMATION FOR SEQ ID NO:9:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Gln Pro Ile Asp Asp Thr Glu Ser Asn Thr Thr Ser Val Asn Leu Met
1               5                   10                  15
Ala ( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Gln Pro Ile Asp Asp Thr Glu Ser Asn Thr Thr Ser Val Asn Val Pro
1               5                   10                  15
Thr ( 2 ) INFORMATION FOR SEQ ID NO:11:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Gln Pro Ile Asp Asp Thr Glu Ser Asn Thr Thr Leu Val Asn Val Pro
1               5                   10                  15
Thr ( 2 ) INFORMATION FOR SEQ ID NO:12:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Gln Pro Ile Asp Asp Thr Glu Ser Asn Thr Thr Ser Val Asn Leu Pro
1               5                   10                  15
Thr ( 2 ) INFORMATION FOR SEQ ID NO:13:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Gln Pro Ile Asp Asp Thr Glu Ser Asn Thr Thr Leu Val Asn Val Pro
1               5                   10                  15
Gly Ala ( 2 ) INFORMATION FOR SEQ ID NO:14:

( i ) SEQUENCE CHARACTERISTICS:
        ( A ) LENGTH: 21 amino acids (B) TYPE: amino acid
(D) TOPOLOGY: linear (ii) MOLECULE TYPE: peptide (xi) SEQUENCE DESCRIPTION: SEQ ID NO:14:

Gln Pro Ile Asp Asp Thr Glu Ser Asn Thr Thr Ser Val Asn Leu Met
1               5                   10                  15
Ala Pro Ala Val Ala
            20

(2) INFORMATION FOR SEQ ID NO:15:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:15:

Gln Pro Ile Asp Asp Thr Glu Ser Asn Thr Thr Ser Val Asn Leu Met
1               5                   10                  15
Asp Leu Ala Val Gly Leu Pro Gly Ala
            20                  25

(2) INFORMATION FOR SEQ ID NO:16:

(i) SEQUENCE CHARACTERISTICS:
    (A) LENGTH: 33 amino acids
    (B) TYPE: amino acid
    (D) TOPOLOGY: linear (ii) MOLECULE TYPE: peptide (xi) SEQUENCE DESCRIPTION: SEQ ID NO:16:

Gln Pro Ile Asp Asp Thr Glu Ser Asn Thr Thr Ser Val Asn Leu Met
1               5                   10                  15
Ala Asp Asp Thr Glu Ser Ile Asn Thr Thr Leu Val Asn Leu Pro Gly
            20                  25                  30
Ala (2) INFORMATION FOR SEQ ID NO:17:

(i) SEQUENCE CHARACTERISTICS:
    (A) LENGTH: 19 amino acids
    (B) TYPE: amino acid
    (D) TOPOLOGY: linear (ii) MOLECULE TYPE: peptide (xi) SEQUENCE DESCRIPTION: SEQ ID NO:17:

Gln Pro Ile Asp Asp Thr Glu Ser Ile Asn Thr Thr Leu Val Asn Leu
1               5                   10                  15
Pro Gly Ala (2) INFORMATION FOR SEQ ID NO:18:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (xi) SEQUENCE DESCRIPTION: SEQ ID NO:18:

```
Gln Pro Ile Asp Asp Thr Glu Ser Asn Thr Thr Leu Val Asn Leu Pro
1               5                   10                  15
Gly Ala
```

( 2 ) INFORMATION FOR SEQ ID NO:19:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Gln Pro Ile Asp Asp Thr Glu Ser Asn Thr Thr Ser Val Asn Leu Met
1               5                   10                  15
Ala Asp Asp Thr Glu Ser Arg Phe Ala Thr Asn Thr Thr Leu Val Asn
                20                  25                  30
Leu Pro Leu
        35
```

( 2 ) INFORMATION FOR SEQ ID NO:20:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Gln Pro Ile Asp Asp Thr Glu Ser Asn Thr Thr Ser Val Asn Leu Met
1               5                   10                  15
Ala Asp Asp Thr Glu Ser Ile Asn Thr Thr Leu Val Asn Leu Ala Asn
                20                  25                  30
Val Ala Met Ala
        35
```

( 2 ) INFORMATION FOR SEQ ID NO:21:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Gln Pro Ile Asp Asp Thr Glu Ser Ala Ile Asn Thr Thr Leu Val Asn
1               5                   10                  15
Leu Pro Gly Ala
        20
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Gln Pro Ile Asp Asp Thr Glu Ser Phe Ala Thr Asn Thr Thr Leu Val
1               5                   10                  15
```

Asn Leu Pro Gly Ala
            20

( 2 ) INFORMATION FOR SEQ ID NO:23:

( i ) SEQUENCE CHARACTERISTICS:
        ( A ) LENGTH: 36 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Gln Pro Ile Asp Asp Thr Glu Ser Ile Asn Thr Thr Leu Val Asn Leu
1               5                   10                  15

Met Ala Asp Asp Thr Glu Ser Arg Phe Ala Thr Asn Thr Thr Leu Val
            20                  25                  30

Asn Leu Pro Leu
        35

( 2 ) INFORMATION FOR SEQ ID NO:24:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Gln Pro Ile Asp Asp Thr Glu Ser Ile Asn Thr Thr Leu Val Asn Leu
1               5                   10                  15

Met Ala Asp Asp Thr Glu Ser Arg Phe Ala Thr Asn Thr Thr Leu Asp
            20                  25                  30

Val Val Asn Leu Pro Gly Ala
            35

( 2 ) INFORMATION FOR SEQ ID NO:25:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Gln Pro Ile Asp Asp Thr Glu Ser Ala Ala Ile Asn Thr Thr Leu Val
1               5                   10                  15

Asn Leu Pro Gly Ala
            20

( 2 ) INFORMATION FOR SEQ ID NO:26:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Leu Val Asn
            20                  25                  30

Leu Ala Asn Val Ala Met Ala
            35

(2) INFORMATION FOR SEQ ID NO:27:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (xi) SEQUENCE DESCRIPTION: SEQ ID NO:27:

Gln Pro Ile Asp Asp Thr Glu Ser Asn Thr Thr Ser Val Asn Leu Met
1               5                   10                  15

Ala Asp Asp Thr Glu Ser Arg Phe Ala Thr Asn Thr Thr Leu Asp Val
            20                  25                  30

Val Asn Leu Ile Ser Met Ala
            35

(2) INFORMATION FOR SEQ ID NO:28:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (xi) SEQUENCE DESCRIPTION: SEQ ID NO:28:

Gln Pro Ile Asp Asp Thr Glu Ser Asn Thr Thr Ser Val Asn Leu Met
1               5                   10                  15

Ala Asn Thr Thr Glu Ser Arg Phe Ala Thr Asn Thr Thr Leu Asp Val
            20                  25                  30

Val Asn Leu Ile Ser Met Ala
            35

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TAAATCTATA ACTACAAAAA ACACATA                                                    27

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GACTCTCTTA ACTGGCAAGT TGACA                                                      25

(2) INFORMATION FOR SEQ ID NO:31:

(i) SEQUENCE CHARACTERISTICS:

( A ) LENGTH: 56 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:31:

AAGTACAAAG CTTCAACCAA GTGAGAACCA CACAAGTGTT GGTTAACGAA TCTCTT     56

( 2 ) INFORMATION FOR SEQ ID NO:32:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:32:

CATACACAAT ATAAACGACG G     21

( 2 ) INFORMATION FOR SEQ ID NO:33:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:33:

GAATCTCTTA GCTGGCAAGT TGACAGAAGT AGTGTTAGTT TCAGAGTCGT CAATT     55

( 2 ) INFORMATION FOR SEQ ID NO:34:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:34:

AACGAATCTC TTAGCACCTG GCAAGTTGAC AGAAGT     36

( 2 ) INFORMATION FOR SEQ ID NO:35:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:35:

AACGAATCTC TTAGCACCTG GCAAGTTGAC CAAAGTAGTG TTGATAGATT CAGTGTCGTC     60

( 2 ) INFORMATION FOR SEQ ID NO:36:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:36:

| AACGAATCTC | TTAGCACCTG | GCAAGTTAAC | CAAAGTAGTG | TTGATAGATT | CAGTGTCGTC | 60 |
| AGCCATCAAG | TTGAC | | | | | 75 |

( 2 ) INFORMATION FOR SEQ ID NO:37:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

| AACGAATCTC | TTCAATGGCA | AGTTAACCAA | AGTAGTGTTA | GTAGCGAATC | TAGATTCAGT | 60 |
| GTCGTCAGCC | AT | | | | | 72 |

( 2 ) INFORMATION FOR SEQ ID NO:38:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

| AACGAATCTC | TTAGCCATGG | CAACGTTAGC | CAAGTTAACC | AAAGT | 45 |

( 2 ) INFORMATION FOR SEQ ID NO:39:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

| AACGAATCTC | TTAGCACCTG | GCAAGTTGAC | CAAAGTAGTG | TTGATAGCAG | ATTCAGTGTC | 60 |
| G | | | | | | 61 |

( 2 ) INFORMATION FOR SEQ ID NO:40:

( i ) SEQUENCE CHARACTERISTICS:
        ( A ) LENGTH: 372 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 82..351

( i x ) FEATURE:
        ( A ) NAME/KEY: misc_feature
        ( B ) LOCATION: 1..372
        ( D ) OTHER INFORMATION: /note= "complementary strand"

( x i ) SEQUENCE DESCRIPTION: SEQ ID NO:40:

| GAATTCATTC | AAGAATAGTT | CAAACAAGAA | GATTACAAAC | TATCAATTTC | ATACACAATA | 60 |

| | | | | | | | | | | | | | | | |
|---|---|---|---|---|---|---|---|---|---|---|---|---|---|---|---|
|TAAACGACGG|GTACCAAAAT|A|ATG|AAA|CTG|AAA|ACT|GTA|AGA|TCT|GCG|GTC| | |111|
| | | |Met|Lys|Leu|Lys|Thr|Val|Arg|Ser|Ala|Val| | | |
| | | |1| | | |5| | | | |10| | | |
|CTT|TCG|TCA|CTC|TTT|GCA|TCT|CAG|GTC|CTT|GGC|CAA|CCA|ATA|GAC GAA|159|
|Leu|Ser|Ser|Leu|Phe|Ala|Ser|Gln|Val|Leu|Gly|Gln|Pro|Ile|Asp Glu| |
| | | | |15| | | |20| | | | |25| | |
|GAC|AAC|GAC|ACT|TCT|TCC|ATG|GCT|AAG|AGA|TTC|GTT|AAC|CAA|CAC TTG|207|
|Asp|Asn|Asp|Thr|Ser|Ser|Met|Ala|Lys|Arg|Phe|Val|Asn|Gln|His Leu| |
| | |30| | | | |35| | | | |40| | | |
|TGC|GGT|TCC|CAC|TTG|GTT|GAA|GCT|TTG|TAC|TTG|GTT|TGC|GGT|GAA AGA|255|
|Cys|Gly|Ser|His|Leu|Val|Glu|Ala|Leu|Tyr|Leu|Val|Cys|Gly|Glu Arg| |
| | |45| | | | |50| | | | |55| | | |
|GGT|TTC|TTC|TAC|ACT|CCT|AAG|GCT|GCT|AAG|GGT|ATT|GTC|GAG|CAA TGC|303|
|Gly|Phe|Phe|Tyr|Thr|Pro|Lys|Ala|Ala|Lys|Gly|Ile|Val|Glu|Gln Cys| |
| |60| | | | |65| | | | |70| | | | |
|TGT|ACC|TCC|ATC|TGC|TCC|TTG|TAC|CAA|TTG|GAA|AAC|TAC|TGC|AAC TAG|358|
|Cys|Thr|Ser|Ile|Cys|Ser|Leu|Tyr|Gln|Leu|Glu|Asn|Tyr|Cys|Asn| |
|75| | | | |80| | | | |85| | | | |90|
|ACGCAGCCCG|CAGGCTC|TAGA| | | | | | | | | | | | |372|

( 2 ) INFORMATION FOR SEQ ID NO:41:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Met Lys Leu Lys Thr Val Arg Ser Ala Val Leu Ser Ser Leu Phe Ala
1               5                   10                  15

Ser Gln Val Leu Gly Gln Pro Ile Asp Glu Asp Asn Asp Thr Ser Ser
            20                  25                  30

Met Ala Lys Arg Phe Val Asn Gln His Leu Cys Gly Ser His Leu Val
        35                  40                  45

Glu Ala Leu Tyr Leu Val Cys Gly Glu Arg Gly Phe Phe Tyr Thr Pro
    50                  55                  60

Lys Ala Ala Lys Gly Ile Val Glu Gln Cys Cys Thr Ser Ile Cys Ser
65                  70                  75                  80

Leu Tyr Gln Leu Glu Asn Tyr Cys Asn
                85

( 2 ) INFORMATION FOR SEQ ID NO:42:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..45

( i x ) FEATURE:
        ( A ) NAME/KEY: misc_feature
        ( B ) LOCATION: 1..45
        ( D ) OTHER INFORMATION: /note= "complementary strand"

( x i ) SEQUENCE DESCRIPTION: SEQ ID NO:42:

CAA CCA ATT GAC GAC GAA AAC ACT ACT TCT GTC AAC TTG CCA GTT    45

```
Gln  Pro  Ile  Asp  Asp  Glu  Asn  Thr  Thr  Ser  Val  Asn  Leu  Pro  Val
 1              5                        10                        15
```

( 2 ) INFORMATION FOR SEQ ID NO:43:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

```
Gln  Pro  Ile  Asp  Asp  Glu  Asn  Thr  Thr  Ser  Val  Asn  Leu  Pro  Val
 1              5                        10                        15
```

( 2 ) INFORMATION FOR SEQ ID NO:44:

( i ) SEQUENCE CHARACTERISTICS:
        ( A ) LENGTH: 297 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..276

( i x ) FEATURE:
        ( A ) NAME/KEY: misc_feature
        ( B ) LOCATION: 1..297
        ( D ) OTHER INFORMATION: /note= "complementary strand"

( x i ) SEQUENCE DESCRIPTION: SEQ ID NO:44:

```
ATG  AAA  CTG  AAA  ACT  GTA  AGA  TCT  GCG  GTC  CTT  TCG  TCA  CTC  TTT  GCA      48
Met  Lys  Leu  Lys  Thr  Val  Arg  Ser  Ala  Val  Leu  Ser  Ser  Leu  Phe  Ala
 1              5                        10                       15

TCT  CAG  GTC  CTT  GGC  CAA  CCA  ATT  GAC  GAC  GAA  AAC  ACT  ACT  TCT  GTC      96
Ser  Gln  Val  Leu  Gly  Gln  Pro  Ile  Asp  Asp  Glu  Asn  Thr  Thr  Ser  Val
                20                       25                       30

AAC  TTG  CCA  GTT  AAG  AGA  TTC  GTT  AAC  CAA  CAC  TTG  TGT  GGT  TCT  CAC     144
Asn  Leu  Pro  Val  Lys  Arg  Phe  Val  Asn  Gln  His  Leu  Cys  Gly  Ser  His
           35                       40                       45

TTG  GTT  GAA  GCT  TTG  TAC  TTG  GTT  TGC  GGT  GAA  AGA  GGT  TTC  TTC  TAC     192
Leu  Val  Glu  Ala  Leu  Tyr  Leu  Val  Cys  Gly  Glu  Arg  Gly  Phe  Phe  Tyr
      50                       55                       60

ACT  CCT  AAG  GCT  GCT  AAG  GGT  ATT  GTC  GAA  CAA  TGC  TGT  ACC  TCC  ATC     240
Thr  Pro  Lys  Ala  Ala  Lys  Gly  Ile  Val  Glu  Gln  Cys  Cys  Thr  Ser  Ile
 65                       70                       75                       80

TGC  TCC  TTG  TAC  CAA  TTG  GAA  AAC  TAC  TGC  AAC      TAGACGCAGC  CCGCAGGCTC   293
Cys  Ser  Leu  Tyr  Gln  Leu  Glu  Asn  Tyr  Cys  Asn
                     85                       90

TAGA                                                                                297
```

( 2 ) INFORMATION FOR SEQ ID NO:45:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

```
Met  Lys  Leu  Lys  Thr  Val  Arg  Ser  Ala  Val  Leu  Ser  Ser  Leu  Phe  Ala
 1              5                        10                       15
```

```
Ser Gln Val Leu Gly Gln Pro Ile Asp Asp Glu Asn Thr Thr Ser Val
         20                  25                  30

Asn Leu Pro Val Lys Arg Phe Val Asn Gln His Leu Cys Gly Ser His
         35                  40                  45

Leu Val Glu Ala Leu Tyr Leu Val Cys Gly Glu Arg Gly Phe Phe Tyr
         50                  55                  60

Thr Pro Lys Ala Ala Lys Gly Ile Val Glu Gln Cys Cys Thr Ser Ile
 65                  70                  75                  80

Cys Ser Leu Tyr Gln Leu Glu Asn Tyr Cys Asn
                 85                  90
```

( 2 ) INFORMATION FOR SEQ ID NO:46:

( i ) SEQUENCE CHARACTERISTICS:
    ( A ) LENGTH: 51 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..51

( i x ) FEATURE:
    ( A ) NAME/KEY: misc_feature
    ( B ) LOCATION: 1..51
    ( D ) OTHER INFORMATION: /note= "complementary strand"

( x i ) SEQUENCE DESCRIPTION: SEQ ID NO:46:

```
CAA CCA ATT GAC GAC ACT GAA TCT AAC ACT ACT TCT GTC AAC TTG CCA        48
Gln Pro Ile Asp Asp Thr Glu Ser Asn Thr Thr Ser Val Asn Leu Pro
 1               5                  10                  15

GCT                                                                     51
Ala
```

( 2 ) INFORMATION FOR SEQ ID NO:47:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:47:

```
Gln Pro Ile Asp Asp Thr Glu Ser Asn Thr Thr Ser Val Asn Leu Pro
 1               5                  10                  15

Ala
```

( 2 ) INFORMATION FOR SEQ ID NO:48:

( i ) SEQUENCE CHARACTERISTICS:
    ( A ) LENGTH: 54 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 1..54

( i x ) FEATURE:
    ( A ) NAME/KEY: misc_feature
    ( B ) LOCATION: 1..54

( D ) OTHER INFORMATION: /note= "complementary strand"

( x i ) SEQUENCE DESCRIPTION: SEQ ID NO:48:

| CAA | CCA | ATT | GAC | GAC | ACT | GAA | TCT | AAC | ACT | ACT | TCT | GTC | AAC | TTG | CCA | 48 |
| Gln | Pro | Ile | Asp | Asp | Thr | Glu | Ser | Asn | Thr | Thr | Ser | Val | Asn | Leu | Pro | |
| 1 | | | | 5 | | | | | 10 | | | | | 15 | | |

| GGT | GCT | | | | | | | | | | | | | | | 54 |
| Gly | Ala | | | | | | | | | | | | | | | |

( 2 ) INFORMATION FOR SEQ ID NO:49:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..57

( i x ) FEATURE:
        ( A ) NAME/KEY: misc_feature
        ( B ) LOCATION: 1..57
        ( D ) OTHER INFORMATION: /note= "complementary strand"

( x i ) SEQUENCE DESCRIPTION: SEQ ID NO:49:

| CAA | CCA | ATT | GAC | GAC | ACT | GAA | TCT | ATC | AAC | ACT | ACT | TTG | GTC | AAC | TTG | 48 |
| Gln | Pro | Ile | Asp | Asp | Thr | Glu | Ser | Ile | Asn | Thr | Thr | Leu | Val | Asn | Leu | |
| 1 | | | | 5 | | | | | 10 | | | | | 15 | | |

| CCA | GGT | GCT | | | | | | | | | | | | | | 57 |
| Pro | Gly | Ala | | | | | | | | | | | | | | |

( 2 ) INFORMATION FOR SEQ ID NO:50:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..99

( i x ) FEATURE:
        ( A ) NAME/KEY: misc_feature
        ( B ) LOCATION: 1..99
        ( D ) OTHER INFORMATION: /note= "complementary strand"

( x i ) SEQUENCE DESCRIPTION: SEQ ID NO:50:

| CAA | CCA | ATT | GAC | GAC | ACT | GAA | TCT | AAC | ACT | ACT | TCT | GTC | AAC | TTG | ATG | 48 |
| Gln | Pro | Ile | Asp | Asp | Thr | Glu | Ser | Asn | Thr | Thr | Ser | Val | Asn | Leu | Met | |
| 1 | | | | 5 | | | | | 10 | | | | | 15 | | |

| GCT | GAC | GAC | ACT | GAA | TCT | ATC | AAC | ACT | ACT | TTG | GTT | AAC | TTG | CCA | GGT | 96 |
| Ala | Asp | Asp | Thr | Glu | Ser | Ile | Asn | Thr | Thr | Leu | Val | Asn | Leu | Pro | Gly | |
| | | | 20 | | | | | 25 | | | | | 30 | | | |

| GCT | | | | | | | | | | | | | | | | 99 |
| Ala | | | | | | | | | | | | | | | | |

( 2 ) INFORMATION FOR SEQ ID NO:51:

( i ) SEQUENCE CHARACTERISTICS:
        ( A ) LENGTH: 105 base pairs
        ( B ) TYPE: nucleic acid
        ( C ) STRANDEDNESS: double (D) TOPOLOGY: linear (i i) MOLECULE TYPE: DNA (genomic)

(i x) FEATURE:
    (A) NAME/KEY: CDS
    (B) LOCATION: 1..105

(i x) FEATURE:
    (A) NAME/KEY: misc_feature
    (B) LOCATION: 1..105
    (D) OTHER INFORMATION: /note= "complementary strand"

(x i) SEQUENCE DESCRIPTION: SEQ ID NO:51:

| CAA | CCA | ATT | GAC | GAC | ACT | GAA | TCT | AAC | ACT | ACT | TCT | GTC | AAC | TTG | ATG | 48 |
|---|---|---|---|---|---|---|---|---|---|---|---|---|---|---|---|---|
| Gln | Pro | Ile | Asp | Asp | Thr | Glu | Ser | Asn | Thr | Thr | Ser | Val | Asn | Leu | Met | |
| 1 | | | | 5 | | | | | 10 | | | | | 15 | | |

| GCT | GAC | GAC | ACT | GAA | TCT | AGA | TTC | GCT | ACT | AAC | ACT | ACT | TTG | GTT | AAC | 96 |
|---|---|---|---|---|---|---|---|---|---|---|---|---|---|---|---|---|
| Ala | Asp | Asp | Thr | Glu | Ser | Arg | Phe | Ala | Thr | Asn | Thr | Thr | Leu | Val | Asn | |
| | | | 20 | | | | | 25 | | | | | 30 | | | |

| TTG | CCA | TTG | | | | | | | | | | | | | | 105 |
|---|---|---|---|---|---|---|---|---|---|---|---|---|---|---|---|---|
| Leu | Pro | Leu | | | | | | | | | | | | | | |
| | | 35 | | | | | | | | | | | | | | |

(2) INFORMATION FOR SEQ ID NO:52:

(i) SEQUENCE CHARACTERISTICS:
        (A) LENGTH: 108 base pairs
        (B) TYPE: nucleic acid
        (C) STRANDEDNESS: double
        (D) TOPOLOGY: linear (i i) MOLECULE TYPE: DNA (genomic)

(i x) FEATURE:
        (A) NAME/KEY: CDS
        (B) LOCATION: 1..108

(i x) FEATURE:
        (A) NAME/KEY: misc_feature
        (B) LOCATION: 1..108
        (D) OTHER INFORMATION: /note= "complementary strand"

(x i) SEQUENCE DESCRIPTION: SEQ ID NO:52:

| CAA | CCA | ATT | GAC | GAC | ACT | GAA | TCT | AAC | ACT | ACT | TCT | GTC | AAC | TTG | ATG | 48 |
|---|---|---|---|---|---|---|---|---|---|---|---|---|---|---|---|---|
| Gln | Pro | Ile | Asp | Asp | Thr | Glu | Ser | Asn | Thr | Thr | Ser | Val | Asn | Leu | Met | |
| 1 | | | | 5 | | | | | 10 | | | | | 15 | | |

| GCT | GAC | GAC | ACT | GAA | TCT | ATC | AAC | ACT | ACT | TTG | GTT | AAC | TTG | GCT | AAC | 96 |
|---|---|---|---|---|---|---|---|---|---|---|---|---|---|---|---|---|
| Ala | Asp | Asp | Thr | Glu | Ser | Ile | Asn | Thr | Thr | Leu | Val | Asn | Leu | Ala | Asn | |
| | | | 20 | | | | | 25 | | | | | 30 | | | |

| GTT | GCC | ATG | GCT | | | | | | | | | | | | | 108 |
|---|---|---|---|---|---|---|---|---|---|---|---|---|---|---|---|---|
| Val | Ala | Met | Ala | | | | | | | | | | | | | |
| | | 35 | | | | | | | | | | | | | | |

(2) INFORMATION FOR SEQ ID NO:53:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (i i) MOLECULE TYPE: DNA (genomic)

(i x) FEATURE:
        (A) NAME/KEY: CDS
        (B) LOCATION: 1..60

(i x) FEATURE:
        (A) NAME/KEY: misc_feature
        (B) LOCATION: 1..60
        (D) OTHER INFORMATION: /note= "complementary strand"

( x i ) SEQUENCE DESCRIPTION: SEQ ID NO:53:

| CAA | CCA | ATT | GAC | GAC | ACT | GAA | TCT | GCT | ATC | AAC | ACT | ACT | TTG | GTC | AAC | 48 |
|---|---|---|---|---|---|---|---|---|---|---|---|---|---|---|---|---|
| Gln | Pro | Ile | Asp | Asp | Thr | Glu | Ser | Ala | Ile | Asn | Thr | Thr | Leu | Val | Asn | |
| 1 | | | | 5 | | | | | 10 | | | | | 15 | | |

| TTG | CCA | GGT | GCT | 60 |
|---|---|---|---|---|
| Leu | Pro | Gly | Ala | |
| | | | 20 | |

( 2 ) INFORMATION FOR SEQ ID NO:54:

( i ) SEQUENCE CHARACTERISTICS:
        ( A ) LENGTH: 276 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 113..274

( i x ) FEATURE:
        ( A ) NAME/KEY: misc_feature
        ( B ) LOCATION: 1..276
        ( D ) OTHER INFORMATION: /note= "complementary strand"

( x i ) SEQUENCE DESCRIPTION: SEQ ID NO:54:

TTAAATCTAT AACTACAAAA AACACATACA GGAATTCATT CAAGAATAGT TCAAACAAGA    60

AGATTACAAA CTATCAATTT CATACACAAT ATAAACGACG GGTACCAAAA TA ATG   115
                                                                                                                                                                                                                                                                                                                Met
                                                                                                                                                                                                                                                                                                                   1

| AAA | CTG | AAA | ACT | GTA | AGA | TCT | GCG | GTC | CTT | TCG | TCA | CTC | TTT | GCA | TCT | 163 |
|---|---|---|---|---|---|---|---|---|---|---|---|---|---|---|---|---|
| Lys | Leu | Lys | Thr | Val | Arg | Ser | Ala | Val | Leu | Ser | Ser | Leu | Phe | Ala | Ser | |
| | | | | 5 | | | | | 10 | | | | | 15 | | |

| CAG | GTC | CTT | GGC | CAA | CCA | ATT | GAC | GAC | GAA | AAC | ACT | ACT | TCT | GTT | AAC | 211 |
|---|---|---|---|---|---|---|---|---|---|---|---|---|---|---|---|---|
| Gln | Val | Leu | Gly | Gln | Pro | Ile | Asp | Asp | Glu | Asn | Thr | Thr | Ser | Val | Asn | |
| | | | 20 | | | | | 25 | | | | | 30 | | | |

| TTG | CCA | GCT | AAG | AGA | TTC | GTT | AAC | CAA | CAC | TTG | TGC | GGT | TCC | CAC | TTG | 259 |
|---|---|---|---|---|---|---|---|---|---|---|---|---|---|---|---|---|
| Leu | Pro | Ala | Lys | Arg | Phe | Val | Asn | Gln | His | Leu | Cys | Gly | Ser | His | Leu | |
| | 35 | | | | | 40 | | | | | 45 | | | | | |

| GTT | GAA | GCT | TTG | TAC | TT | 276 |
|---|---|---|---|---|---|---|
| Val | Glu | Ala | Leu | Tyr | | |
| 50 | | | | | | |

( 2 ) INFORMATION FOR SEQ ID NO:55:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:55:

| Met | Lys | Leu | Lys | Thr | Val | Arg | Ser | Ala | Val | Leu | Ser | Ser | Leu | Phe | Ala |
|---|---|---|---|---|---|---|---|---|---|---|---|---|---|---|---|
| 1 | | | | 5 | | | | | 10 | | | | | 15 | |

| Ser | Gln | Val | Leu | Gly | Gln | Pro | Ile | Asp | Asp | Glu | Asn | Thr | Thr | Ser | Val |
|---|---|---|---|---|---|---|---|---|---|---|---|---|---|---|---|
| | | | 20 | | | | | 25 | | | | | 30 | | |

| Asn | Leu | Pro | Ala | Lys | Arg | Phe | Val | Asn | Gln | His | Leu | Cys | Gly | Ser | His |
|---|---|---|---|---|---|---|---|---|---|---|---|---|---|---|---|
| | | | 35 | | | | | 40 | | | | | 45 | | |

| Leu | Val | Glu | Ala | Leu | Tyr |
|---|---|---|---|---|---|
| | 50 | | | | |

( 2 ) INFORMATION FOR SEQ ID NO:56:

( i ) SEQUENCE CHARACTERISTICS:
    ( A ) LENGTH: 282 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 113..280

( i x ) FEATURE:
    ( A ) NAME/KEY: misc_feature
    ( B ) LOCATION: 1..282

( x i ) SEQUENCE DESCRIPTION: SEQ ID NO:56:

```
TTAAATCTAT AACTACAAAA AACACATACA GGAATTCATT CAAGAATAGT TCAAACAAGA          60

AGATTACAAA CTATCAATTT CATACACAAT ATAAACGACG GGTACCAAAA TA ATG           115
                                                         Met
                                                          1

AAA CTG AAA ACT GTA AGA TCT GCG GTC CTT TCG TCA CTC TTT GCA TCT           163
Lys Leu Lys Thr Val Arg Ser Ala Val Leu Ser Ser Leu Phe Ala Ser
          5                  10                  15

CAG GTC CTT GGC CAA CCA ATT GAC GAC ACT GAA TCT AAC ACT ACT TCT           211
Gln Val Leu Gly Gln Pro Ile Asp Asp Thr Glu Ser Asn Thr Thr Ser
         20                  25                  30

GTC AAC TTG CCA GCT AAG AGA TTC GTT AAC CAA CAC TTG TGC GGT TCC           259
Val Asn Leu Pro Ala Lys Arg Phe Val Asn Gln His Leu Cys Gly Ser
         35                  40                  45

CAC TTG GTT GAA GCT TTG TAC TT                                            282
His Leu Val Glu Ala Leu Tyr
 50                  55
```

( 2 ) INFORMATION FOR SEQ ID NO:57:

( i ) SEQUENCE CHARACTERISTICS:
    ( A ) LENGTH: 56 amino acids
    ( B ) TYPE: amino acid
    ( D ) TOPOLOGY: linear ( i i ) MOLECULE TYPE: protein ( x i ) SEQUENCE DESCRIPTION: SEQ ID NO:57:

```
Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
             20                  25                  30

Ser Val Asn Leu Pro Ala Lys Arg Phe Val Asn Gln His Leu Cys Gly
             35                  40                  45

Ser His Leu Val Glu Ala Leu Tyr
             50                  55
```

( 2 ) INFORMATION FOR SEQ ID NO:58:

( i ) SEQUENCE CHARACTERISTICS:
    ( A ) LENGTH: 282 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 113..280

( i x ) FEATURE:
    ( A ) NAME/KEY: misc_feature
    ( B ) LOCATION: 1..282
    ( D ) OTHER INFORMATION: /note= "complementary strand"

( x i ) SEQUENCE DESCRIPTION: SEQ ID NO:58:

```
TTAAATCTAT AACTACAAAA AACACATACA GGAATTCATT CAAGAATAGT TCAAACAAGA         60

AGATTACAAA CTATCAATTT CATACACAAT ATAAACGACG GGTACCAAAA TA ATG           115
                                                           Met
                                                            1

AAA CTG AAA ACT GTA AGA TCT GCG GTC CTT TCG TCA CTC TTT GCA TCT         163
Lys Leu Lys Thr Val Arg Ser Ala Val Leu Ser Ser Leu Phe Ala Ser
              5                  10                  15

CAG GTC CTT GGC CAA CCA ATT GAC GAC ACT GAA TCT AAC ACT ACT TCT         211
Gln Val Leu Gly Gln Pro Ile Asp Asp Thr Glu Ser Asn Thr Thr Ser
         20                  25                  30

GTC AAC TTG ATG GCT AAG AGA TTC GTT AAC CAA CAC TTG TGC GGT TCC         259
Val Asn Leu Met Ala Lys Arg Phe Val Asn Gln His Leu Cys Gly Ser
     35                  40                  45

CAC TTG GTT GAA GCT TTG TAC TT                                          282
His Leu Val Glu Ala Leu Tyr
 50                  55
```

( 2 ) INFORMATION FOR SEQ ID NO:59:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:59:

```
Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
             20                  25                  30

Ser Val Asn Leu Met Ala Lys Arg Phe Val Asn Gln His Leu Cys Gly
         35                  40                  45

Ser His Leu Val Glu Ala Leu Tyr
     50                  55
```

( 2 ) INFORMATION FOR SEQ ID NO:60:

( i ) SEQUENCE CHARACTERISTICS:
        ( A ) LENGTH: 330 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 113..328

( i x ) FEATURE:
        ( A ) NAME/KEY: misc_feature
        ( B ) LOCATION: 1..330
        ( D ) OTHER INFORMATION: /note= "complementary strand"

( x i ) SEQUENCE DESCRIPTION: SEQ ID NO:60:

```
TTAAATCTAT AACTACAAAA AACACATACA GGAATTCATT CAAGAATAGT TCAAACAAGA         60

AGATTACAAA CTATCAATTT CATACACAAT ATAAACGACG GGTACCAAAA TA ATG           115
                                                           Met
```

```
AAA CTG AAA ACT GTA AGA TCT GCG GTC CTT TCG TCA CTC TTT GCA TCT      163
Lys Leu Lys Thr Val Arg Ser Ala Val Leu Ser Ser Leu Phe Ala Ser
          5                  10                      15

CAG GTC CTT GGC CAA CCA ATT GAC GAC ACT GAA TCT AAC ACT ACT TCT      211
Gln Val Leu Gly Gln Pro Ile Asp Asp Thr Glu Ser Asn Thr Thr Ser
         20                  25                  30

GTC AAC TTG ATG GCT GAC GAC ACT GAA TCT ATC AAC ACT ACT TTG GTT      259
Val Asn Leu Met Ala Asp Asp Thr Glu Ser Ile Asn Thr Thr Leu Val
         35                  40                  45

AAC TTG CCA GGT GCT AAG AGA TTC GTT AAC CAA CAC TTG TGC GGT TCC      307
Asn Leu Pro Gly Ala Lys Arg Phe Val Asn Gln His Leu Cys Gly Ser
 50                  55                  60                  65

CAC TTG GTT GAA GCT TTG TAC TT                                       330
His Leu Val Glu Ala Leu Tyr
             70
```

(2) INFORMATION FOR SEQ ID NO:61:

(i) SEQUENCE CHARACTERISTICS:
        (A) LENGTH: 72 amino acids
        (B) TYPE: amino acid
        (D) TOPOLOGY: linear (ii) MOLECULE TYPE: peptide (xi) SEQUENCE DESCRIPTION: SEQ ID NO:61:

```
Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
             20                  25                  30

Ser Val Asn Leu Met Ala Asp Asp Thr Glu Ser Ile Asn Thr Thr Leu
             35                  40                  45

Val Asn Leu Pro Gly Ala Lys Arg Phe Val Asn Gln His Leu Cys Gly
         50                  55                  60

Ser His Leu Val Glu Ala Leu Tyr
 65                  70
```

(2) INFORMATION FOR SEQ ID NO:62:

(i) SEQUENCE CHARACTERISTICS:
        (A) LENGTH: 288 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 113..286

(ix) FEATURE:
        (A) NAME/KEY: misc_feature
        (B) LOCATION: 1..288
        (D) OTHER INFORMATION: /note= "complementary strand"

(xi) SEQUENCE DESCRIPTION: SEQ ID NO:62:

```
TTAAATCTAT AACTACAAAA AACACATACA GGAATTCATT CAAGAATAGT TCAAACAAGA     60

AGATTACAAA CTATCAATTT CATACACAAT ATAAACGACG GGTACCAAAA TA ATG        115
                                                          Met
                                                           1

AAA CTG AAA ACT GTA AGA TCT GCG GTC CTT TCG TCA CTC TTT GCA TCT      163
Lys Leu Lys Thr Val Arg Ser Ala Val Leu Ser Ser Leu Phe Ala Ser
          5                  10                      15
```

```
CAG  GTC  CTT  GGC  CAA  CCA  ATT  GAC  GAC  ACT  GAA  TCT  ATC  AAC  ACT  ACT    211
Gln  Val  Leu  Gly  Gln  Pro  Ile  Asp  Asp  Thr  Glu  Ser  Ile  Asn  Thr  Thr
          20                  25                       30

TTG  GTC  AAC  TTG  CCA  GGT  GCT  AAG  AGA  TTC  GTT  AAC  CAA  CAC  TTG  TGC    259
Leu  Val  Asn  Leu  Pro  Gly  Ala  Lys  Arg  Phe  Val  Asn  Gln  His  Leu  Cys
          35                  40                       45

GGT  TCC  CAC  TTG  GTT  GAA  GCT  TTG  TAC  TT                                   288
Gly  Ser  His  Leu  Val  Glu  Ala  Leu  Tyr
50                       55
```

( 2 ) INFORMATION FOR SEQ ID NO:63:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

```
Met  Lys  Leu  Lys  Thr  Val  Arg  Ser  Ala  Val  Leu  Ser  Ser  Leu  Phe  Ala
1                   5                        10                      15

Ser  Gln  Val  Leu  Gly  Gln  Pro  Ile  Asp  Asp  Thr  Glu  Ser  Ile  Asn  Thr
          20                  25                       30

Thr  Leu  Val  Asn  Leu  Pro  Gly  Ala  Lys  Arg  Phe  Val  Asn  Gln  His  Leu
          35                  40                       45

Cys  Gly  Ser  His  Leu  Val  Glu  Ala  Leu  Tyr
50                       55
```

( 2 ) INFORMATION FOR SEQ ID NO:64:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
GGTTAACGAA  CTTTGGAGCT  TCAGCTTCAG  CTTCTTCTCT  CTTAGCCATG  GAGATCAAGT    60

TAACAACATC  CAAAGTAGTG  TT                                                82
```

( 2 ) INFORMATION FOR SEQ ID NO:65:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

```
CAAGTACAAA  GCTTCAACCA  AGTGGGAACC  GCACAAGTGT  TGGTTAACGA  ACTT          54
```

( 2 ) INFORMATION FOR SEQ ID NO:66:

( i ) SEQUENCE CHARACTERISTICS:
        ( A ) LENGTH: 117 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..117

( i x ) FEATURE:
        ( A ) NAME/KEY: misc_feature ( B ) LOCATION: 1..117
( D ) OTHER INFORMATION: /note= "complementary strand"

( x i ) SEQUENCE DESCRIPTION: SEQ ID NO:66:

| CAA | CCA | ATT | GAC | GAC | ACT | GAA | TCT | AAC | ACT | ACT | TCT | GTC | AAC | TTG | ATG | 48 |
| Gln | Pro | Ile | Asp | Asp | Thr | Glu | Ser | Asn | Thr | Thr | Ser | Val | Asn | Leu | Met | |
| 1 | | | | 5 | | | | | 10 | | | | | 15 | | |

| GCT | GAC | GAC | ACT | GAA | TCT | AGA | TTC | GCT | ACT | AAC | ACT | ACT | TTG | GAT | GTT | 96 |
| Ala | Asp | Asp | Thr | Glu | Ser | Arg | Phe | Ala | Thr | Asn | Thr | Thr | Leu | Asp | Val | |
| | | 20 | | | | | 25 | | | | | 30 | | | | |

| GTT | AAC | TTG | ATC | TCC | ATG | GCT | | | | | | | | | | 117 |
| Val | Asn | Leu | Ile | Ser | Met | Ala | | | | | | | | | | |
| | | 35 | | | | | | | | | | | | | | |

( 2 ) INFORMATION FOR SEQ ID NO:67:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( x i ) SEQUENCE DESCRIPTION: SEQ ID NO:67:

TCTCTTAGCC ATGGAGATCA AGTTAACAAC ATCCAAAGCC AAAGTAGTGT T                51

( 2 ) INFORMATION FOR SEQ ID NO:68:

( i ) SEQUENCE CHARACTERISTICS:
( A ) LENGTH: 123 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..123

( i x ) FEATURE:
( A ) NAME/KEY: misc_feature
( B ) LOCATION: 1..123
( D ) OTHER INFORMATION: /note= "complementary strand"

( x i ) SEQUENCE DESCRIPTION: SEQ ID NO:68:

| CAA | CCA | ATT | GAC | GAC | ACT | GAA | TCT | AAC | ACT | ACT | TCT | GTC | AAC | TTG | ATG | 48 |
| Gln | Pro | Ile | Asp | Asp | Thr | Glu | Ser | Asn | Thr | Thr | Ser | Val | Asn | Leu | Met | |
| 40 | | | | | 45 | | | | | 50 | | | | | 55 | |

| GCT | GAC | GAC | ACT | GAA | TCT | AGA | TTC | GCT | ACT | AAC | ACT | ACT | TTG | GCT | TTG | 96 |
| Ala | Asp | Asp | Thr | Glu | Ser | Arg | Phe | Ala | Thr | Asn | Thr | Thr | Leu | Ala | Leu | |
| | | | | 60 | | | | | 65 | | | | | 70 | | |

| GAT | GTT | GTT | AAC | TTG | ATC | TCC | ATG | GCT | | | | | | | | 123 |
| Asp | Val | Val | Asn | Leu | Ile | Ser | Met | Ala | | | | | | | | |
| | | | 75 | | | | | 80 | | | | | | | | |

( 2 ) INFORMATION FOR SEQ ID NO:69:

( i ) SEQUENCE CHARACTERISTICS:
( A ) LENGTH: 41 amino acids
( B ) TYPE: amino acid
( D ) TOPOLOGY: linear ( i i ) MOLECULE TYPE: protein ( x i ) SEQUENCE DESCRIPTION: SEQ ID NO:69:

| Gln | Pro | Ile | Asp | Asp | Thr | Glu | Ser | Asn | Thr | Thr | Ser | Val | Asn | Leu | Met |
| 1 | | | | 5 | | | | | 10 | | | | | 15 | |

| Ala | Asp | Asp | Thr | Glu | Ser | Arg | Phe | Ala | Thr | Asn | Thr | Thr | Leu | Ala | Leu |
| | | 20 | | | | | 25 | | | | | 30 | | | |

```
Asp Val Val Asn Leu Ile Ser Met Ala
        35                  40
```

( 2 ) INFORMATION FOR SEQ ID NO:70:

( i ) SEQUENCE CHARACTERISTICS:
        ( A ) LENGTH: 219 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..198

( i x ) FEATURE:
        ( A ) NAME/KEY: misc_feature
        ( B ) LOCATION: 1..219
        ( D ) OTHER INFORMATION: /note= "complementary strand"

( x i ) SEQUENCE DESCRIPTION: SEQ ID NO:70:

```
AAG AGA GAA GAA GCT GAA GCT GAA GCT GAA CCA AAG TTC GTT AAC CAA      48
Lys Arg Glu Glu Ala Glu Ala Glu Ala Glu Pro Lys Phe Val Asn Gln
 1               5                  10                  15

CAC TTG TGT GGT TCT CAC TTG GTT GAA GCT TTG TAC TTG GTT TGC GGT      96
His Leu Cys Gly Ser His Leu Val Glu Ala Leu Tyr Leu Val Cys Gly
            20                  25                  30

GAA AGA GGT TTC TTC TAC ACT CCT AAG GCT GCT AAG GGT ATT GTC GAA     144
Glu Arg Gly Phe Phe Tyr Thr Pro Lys Ala Ala Lys Gly Ile Val Glu
        35                  40                  45

CAA TGC TGT ACC TCC ATC TGC TCC TTG TAC CAA TTG GAA AAC TAC TGC     192
Gln Cys Cys Thr Ser Ile Cys Ser Leu Tyr Gln Leu Glu Asn Tyr Cys
    50                  55                  60

AAC TAG ACGCAGCCG CAGGCTCTAG A                                      219
Asn *
 65
```

( 2 ) INFORMATION FOR SEQ ID NO:71:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

```
Lys Arg Glu Glu Ala Glu Ala Glu Ala Glu Pro Lys Phe Val Asn Gln
 1               5                  10                  15

His Leu Cys Gly Ser His Leu Val Glu Ala Leu Tyr Leu Val Cys Gly
            20                  25                  30

Glu Arg Gly Phe Phe Tyr Thr Pro Lys Ala Ala Lys Gly Ile Val Glu
        35                  40                  45

Gln Cys Cys Thr Ser Ile Cys Ser Leu Tyr Gln Leu Glu Asn Tyr Cys
    50                  55                  60

Asn
 65
```

( 2 ) INFORMATION FOR SEQ ID NO:72:

( i ) SEQUENCE CHARACTERISTICS:
        ( A ) LENGTH: 348 base pairs
        ( B ) TYPE: nucleic acid
        ( C ) STRANDEDNESS: double
        ( D ) TOPOLOGY: linear ( i x ) FEATURE:
    ( A ) NAME/KEY: CDS
    ( B ) LOCATION: 113..346

( i x ) FEATURE:
    ( A ) NAME/KEY: misc_feature
    ( B ) LOCATION: 1..348
    ( D ) OTHER INFORMATION: /note= "complementary strand"

( x i ) SEQUENCE DESCRIPTION: SEQ ID NO:72:

```
TTAAATCTAT AACTACAAAA AACACATACA GGAATTCCAT TCAAGAATAG TTCAAACAAG        60

AAGATTACAA ACTATCAATT TCATACACAA TATAAACGAC GGTACCAAAA TA ATG          115
                                                         Met
                                                          1 5

AAA CTG AAA ACT GTA AGA TCT GCG GTC CTT TCG TCA CTC TTT GCA TCT        163
Lys Leu Lys Thr Val Arg Ser Ala Val Leu Ser Ser Leu Phe Ala Ser
             20              25                  30

CAG GTC CTT GGC CAA CCA ATT GAC GAC ACT GAA TCT AAC ACT ACT TCT        211
Gln Val Leu Gly Gln Pro Ile Asp Asp Thr Glu Ser Asn Thr Thr Ser
             35              40                  45

GTC AAC TTG ATG GCT GAC GAC ACT GAA TCT AGA TTC GCT ACT AAC ACT        259
Val Asn Leu Met Ala Asp Asp Thr Glu Ser Arg Phe Ala Thr Asn Thr
         50              55                  60

ACT TTG GTT AAC TTG GCT AAC GTT GCC AAC CAA CAC TTG TGT GGT TCT        307
Thr Leu Val Asn Leu Ala Asn Val Ala Asn Gln His Leu Cys Gly Ser
     65              70                  75

CAC TTG GTT GAA GCT TTG TAC TTA TGG CTA AGA GAT TCG TT                 348
His Leu Val Glu Ala Leu Tyr Leu Trp Leu Arg Asp Ser
 80              85                  90
```

( 2 ) INFORMATION FOR SEQ ID NO:73:

( i ) SEQUENCE CHARACTERISTICS:
    ( A ) LENGTH: 78 amino acids
    ( B ) TYPE: amino acid
    ( D ) TOPOLOGY: linear ( i i ) MOLECULE TYPE: protein ( x i ) SEQUENCE DESCRIPTION: SEQ ID NO:73:

```
Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
             20                  25                  30

Ser Val Asn Leu Met Ala Asp Asp Thr Glu Ser Arg Phe Ala Thr Asn
         35                  40                  45

Thr Thr Leu Val Asn Leu Ala Asn Val Ala Asn Gln His Leu Cys Gly
     50                  55                  60

Ser His Leu Val Glu Ala Leu Tyr Leu Trp Leu Arg Asp Ser
 65                  70                  75
```

( 2 ) INFORMATION FOR SEQ ID NO:74:

( i ) SEQUENCE CHARACTERISTICS:
    ( A ) LENGTH: 379 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 113..376

( i x ) FEATURE:
    ( A ) NAME/KEY: misc_feature
    ( B ) LOCATION: 1..379

( D ) OTHER INFORMATION: /note= "complementary strand"

( x i ) SEQUENCE DESCRIPTION: SEQ ID NO:74:

| TTAAATCTAT | AACTACAAAA | AACACATACA | GGAATTCCAT | TCAAGAATAG | TTCAAACAAG | 60 |

| AAGATTACAA | ACTATCAATT | TCATACACAA | TATAAACGAC | GGTACCAAAA | TA ATG | 115 |
|   |   |   |   |   | Met |   |

| AAA | CTG | AAA | ACT | GTA | AGA | TCT | GCG | GTC | CTT | TCG | TCA | CTC | TTT | GCA | TCT | 163 |
| Lys | Leu | Lys | Thr | Val | Arg | Ser | Ala | Val | Leu | Ser | Ser | Leu | Phe | Ala | Ser |   |
| 80 |   |   |   |   | 85 |   |   |   |   | 90 |   |   |   |   | 95 |   |

| CAG | GTC | CTT | GGC | CAA | CCA | ATT | GAC | GAC | ACT | GAA | TCT | AAC | ACT | ACT | TCT | 211 |
| Gln | Val | Leu | Gly | Gln | Pro | Ile | Asp | Asp | Thr | Glu | Ser | Asn | Thr | Thr | Ser |   |
|   |   |   |   | 100 |   |   |   |   | 105 |   |   |   |   | 110 |   |   |

| GTC | AAC | TTG | ATG | GCT | GAC | GAC | ACT | GAA | TCT | AGA | TTC | GCT | ACT | AAC | ACT | 259 |
| Val | Asn | Leu | Met | Ala | Asp | Asp | Thr | Glu | Ser | Arg | Phe | Ala | Thr | Asn | Thr |   |
|   |   |   | 115 |   |   |   |   | 120 |   |   |   |   | 125 |   |   |   |

| ACT | TTG | GAT | GTT | GTT | AAC | TTG | ATC | TCC | ATG | GCT | AAG | AGA | GAA | GAA | GCT | 307 |
| Thr | Leu | Asp | Val | Val | Asn | Leu | Ile | Ser | Met | Ala | Lys | Arg | Glu | Glu | Ala |   |
|   |   | 130 |   |   |   |   | 135 |   |   |   |   | 140 |   |   |   |   |

| GAA | GCT | GAA | GCT | GAA | CCA | AAG | TTC | GTT | AAC | CAA | CAC | TTG | TGT | GGT | TCT | 355 |
| Glu | Ala | Glu | Ala | Glu | Pro | Lys | Phe | Val | Asn | Gln | His | Leu | Cys | Gly | Ser |   |
| 145 |   |   |   |   | 150 |   |   |   |   | 155 |   |   |   |   |   |   |

| CAC | TTG | GTT | GAA | GCT | TTG | TAC | TTG |   |   |   |   |   |   |   |   | 379 |
| His | Leu | Val | Glu | Ala | Leu | Tyr |   |   |   |   |   |   |   |   |   |   |
| 160 |   |   |   |   | 165 |   |   |   |   |   |   |   |   |   |   |   |

( 2 ) INFORMATION FOR SEQ ID NO:75:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: protein ( x i ) SEQUENCE DESCRIPTION: SEQ ID NO:75:

| Met | Lys | Leu | Lys | Thr | Val | Arg | Ser | Ala | Val | Leu | Ser | Ser | Leu | Phe | Ala |
| 1 |   |   |   | 5 |   |   |   |   | 10 |   |   |   |   | 15 |   |

| Ser | Gln | Val | Leu | Gly | Gln | Pro | Ile | Asp | Asp | Thr | Glu | Ser | Asn | Thr | Thr |
|   |   |   | 20 |   |   |   |   | 25 |   |   |   |   | 30 |   |   |

| Ser | Val | Asn | Leu | Met | Ala | Asp | Asp | Thr | Glu | Ser | Arg | Phe | Ala | Thr | Asn |
|   |   |   | 35 |   |   |   |   | 40 |   |   |   |   | 45 |   |   |

| Thr | Thr | Leu | Asp | Val | Val | Asn | Leu | Ile | Ser | Met | Ala | Lys | Arg | Glu | Glu |
|   |   | 50 |   |   |   |   | 55 |   |   |   |   | 60 |   |   |   |

| Ala | Glu | Ala | Glu | Ala | Glu | Pro | Lys | Phe | Val | Asn | Gln | His | Leu | Cys | Gly |
| 65 |   |   |   |   | 70 |   |   |   |   | 75 |   |   |   |   | 80 |

| Ser | His | Leu | Val | Glu | Ala | Leu | Tyr |
|   |   |   |   | 85 |   |   |   |

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

| Lys | Arg | Glu | Ala | Glu | Ala |
| 1 |   |   |   | 5 |   |

( 2 ) INFORMATION FOR SEQ ID NO:77:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

```
Gln  Pro  Ile  Xaa  Xaa  Xaa  Xaa  Xaa  Asn  Xaa  Xaa  Xaa
 1              5                         10
```

( 2 ) INFORMATION FOR SEQ ID NO:78:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Leu  Val  Asn  Leu  Met  Ala  Asp  Asp  Thr  Glu  Ser  Ile
 1              5                         10
```

( 2 ) INFORMATION FOR SEQ ID NO:79:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Asn  Ser  Thr  Leu  Asn  Leu
 1              5
```

( 2 ) INFORMATION FOR SEQ ID NO:80:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Asn  Thr  Thr  Leu  Asn  Leu
 1              5
```

( 2 ) INFORMATION FOR SEQ ID NO:81:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

```
Asn  Thr  Thr  Leu  Val  Asn  Leu
 1              5
```

( 2 ) INFORMATION FOR SEQ ID NO:82:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:82:

```
Asn  Ser  Thr  Leu  Val  Asn  Leu
 1                    5
```

( 2 ) INFORMATION FOR SEQ ID NO:83:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

```
Leu  Asp  Val  Val  Asn  Leu  Pro  Gly
 1                    5
```

( 2 ) INFORMATION FOR SEQ ID NO:84:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

```
Gly  Ala  Asp  Ser  Lys  Thr  Val  Glu
 1                    5
```

( 2 ) INFORMATION FOR SEQ ID NO:85:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

```
Glu  Glu  Ala  Glu  Ala  Glu  Ala  Pro  Lys
 1                    5
```

( 2 ) INFORMATION FOR SEQ ID NO:86:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

```
Glu  Glu  Ala  Glu  Ala  Glu  Ala  Glu  Pro  Lys
 1                    5                    10
```

(2) INFORMATION FOR SEQ ID NO:87:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:87:

Glu Glu Ala Glu Ala Glu Ala Pro Lys
1               5

(2) INFORMATION FOR SEQ ID NO:88:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:88:

Glu Glu Ala Glu Ala Glu Ala Glu Pro Lys
1               5                   10

(2) INFORMATION FOR SEQ ID NO:89:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:89:

Ile Glu Gly Arg
1

SYNTHETIC LEADER PEPTIDE SEQUENCES

CROSS-REFERENCE TO RELATED APPLICATIONS

This application is a continuation-in-part of application Ser. No. 08/282,852 filed Jul. 29, 1994, now abandoned, which is incorporated herein by reference.

FIELD OF INVENTION

The present invention relates to synthetic leader peptide sequences for secreting polypeptides in yeast.

BACKGROUND OF THE INVENTION

Yeast organisms produce a number of proteins which are synthesized intracellularly, but which have a function outside the cell. Such extracellular proteins are referred to as secreted proteins. These secreted proteins are expressed initially inside the cell in a precursor or a pre-protein form containing a presequence ensuring effective direction of the expressed product across the membrane of the endoplasmic reticulum (ER). The presequence, normally named a signal peptide, is generally cleaved off from the desired product during translocation. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeifer, S. R. and Rothman, J. E. Ann. Rev. Biochem. 56 (1987) 829–852).

Several approaches have been suggested for the expression and secretion in yeast of proteins heterologous to yeast. European published patent application No. 88 632 describes a process by which proteins heterologous to yeast are expressed, processed and secreted by transforming a yeast organism with an expression vehicle harbouring DNA encoding the desired protein and a signal peptide, preparing a culture of the transformed organism, growing the culture and recovering the protein from the culture medium. The signal peptide may be the signal peptide of the desired protein itself, a heterologous signal peptide or a hybrid of native and heterologous signal peptide.

A problem encountered with the use of signal peptides heterologous to yeast might be that the heterologous signal peptide does not ensure efficient translocation and/or cleavage after the signal peptide.

The *Saccharomyces cerevisiae* MFαI (α-factor) is synthesized as a prepro form of 165 amino acids comprising signal- or prepeptide of 19 amino acids followed by a "leader" or propeptide of 64 amino acids, encompassing three N-linked glycosylation sites followed by (LysArg( (Asp/Glu)Ala)$_{2-3}$α-factor)$_4$ (Kurjan, J. and Herskowitz, I. *Cell* 30 (1982) 933–943). The signal-leader part of the preproMFα1 has been widely employed to obtain synthesis and secretion of heterologous proteins in *S. cerevisiae*.

Use of signal/leader peptides homologous to yeast is known from i.a. U.S. patent specification No. 4,546,082, European published patent applications Nos. 116 201, 123 294, 123 544, 163 529 and 123 289 and DK patent application No. 3614/83.

In EP 123 289 utilization of the *S. cerevisiae* a-factor precursor is described whereas WO 84/01153 indicates utilization of the *S. cerevisiae* invertase signal peptide and DK 3614/83 utilization of the *S. cerevisiae* PH05 signal peptide for secretion of foreign proteins.

U.S. patent specification No. 4,546,082, EP 16 201, 123 294, 123 544 and 163 529 describe processes by which the a-factor signal-leader from *S. cerevisiae* (MFα1 or MFα2) is utilized in the secretion process of expressed heterologous proteins in yeast. By fusing a DNA sequence encoding the *S. cerevisiae* MFα1 signal/leader sequence at the 5' end of the gene for the desired protein secretion and processing of the desired protein was demonstrated.

EP 206 783 discloses a system for the secretion of polypeptides from *S. cerevisiae* using an α-factor leader sequence which has been truncated to eliminate the four α-factor units present on the native leader sequence so as to leave the leader peptide itself fused to a heterologous polypeptide via the a-factor processing site LysArgGluAla-GluAla (SEQ ID NO; 76). This construction is indicated to lead to an efficient processing of smaller peptides (less than 50 amino acids). For the secretion and processing of larger polypeptides, the native α-factor leader sequence has been truncated to leave one or two of the α-factor units between the leader peptide and the polypeptide.

A number of secreted proteins are routed so as to be exposed to a proteolytic processing system which can cleave the peptide bond at the carboxy end of two consecutive basic amino acids. This enzymatic activity is in *S. cerevisiae* encoded by the KEX 2 gene (Julius, D. A. et at., *Cell* 37 (1984b) 1075). Processing of the product by the KEX 2 protease is needed for the secretion of active *S. cerevisiae* mating factor α1 (MFα1 or α-factor) whereas KEX 2 is not involved in the secretion of active *S. cerevisiae* mating factor a.

Secretion and correct processing of a polypeptide intended to be secreted is obtained in some cases when culturing a yeast organism which is transformed with a vector constructed as indicated in the references given above. In many cases, however, the level of secretion is very low or there is no secretion, or the proteolytic processing may be incorrect or incomplete. It is therefore the object of the present invention to provide leader peptides which ensure a more efficient expression and/or processing of polypeptides.

SUMMARY OF THE INVENTION

Surprisingly, a new type of leader peptide has been found which allows secretion in high yield of a polypeptide in yeast.

Accordingly, the present invention relates to a DNA expression cassette comprising the following sequence:

5'-P-SP-LS-PS-*gene*-(T)$_t$-3' wherein

P is a promoter sequence,

SP is a DNA sequence encoding a signal peptide,

LS is a DNA sequence encoding a leader peptide with the general formula I:

GlnProIle(Asp/Glu)(Asp/Glu)X$^1$(Glu/Asp)X$^2$AsnZ(Thr/Ser)X$^3$ (SEQ ID NO: 77) (I)

wherein

X$^1$ is a peptide bond or a codable amino acid;

X$^2$ is a peptide bond, a codable amino acid or a sequence of up to 4 codable amino acids which may be the same or different;

Z is a codable amino acid except Pro; and

X$^3$ is a sequence of from 4 to 30 codable amino acids which may be the same or different;

PS is a DNA sequence encoding a processing site;

*gene* is a DNA sequence encoding a polypeptide;

T is a terminator sequence; and i is 0 or 1.

In the present context, the expression "leader peptide" is understood to indicate a peptide whose function is to allow the expressed polypeptide to be directed from the endoplasmic reticulum to the Golgi apparatus and further to a secretory vesicle for secretion into the medium, (i.e. exportation of the expressed polypeptide across the cell wall or at least through the cellular membrane into the periplasmic space of the cell). The term "synthetic" used in connection with leader peptides is intended to indicate that the leader peptide is one not found in nature.

The term "signal peptide" is understood to mean a presequence which is predominantly hydrophobic in nature and present as an N-terminal sequence of the precursor form of an extracellular protein expressed in yeast. The function of the signal peptide is to allow the expressed protein to be secreted to enter the endoplasmic reticulum. The signal peptide is normally cleaved off in the course of this process. The signal peptide may be heterologous or homologous to the yeast organism producing the protein.

The expression "polypeptide" is intended to indicate a heterologous polypeptide, i.e. a polypeptide which is not produced by the host yeast organism in nature as well as a homologous polypeptide, i.e. a polypeptide which is produced by the host yeast organism in nature and any preform thereof. In a preferred embodiment, the expression cassette of the present invention encodes a heterologous polypeptide.

The expression "a codable amino acid" is intended to indicate an amino acid which can be coded for by a triplet ("codon") of nucleotides.

When, in the amino acid sequences given in the present specification, the three letter codes of two amino acids, separated by a slash, are given in brackets, e.g. (Asp/Glu), this is intended to indicate that the sequence has either the one or the other of these amino acids in the pertinent position.

In a further aspect, the present invention relates to a process for producing a polypeptide in yeast, the process comprising culturing a yeast cell, which is capable of expressing a polypeptide and which is transformed with a yeast expression vector as described above including a leader peptide sequence of the invention, in a suitable medium to obtain expression and secretion of the polypeptide, after which the polypeptide is recovered from the medium.

BRIEF DESCRIPTION OF THE DRAWINGS

The present invention is further illustrated with reference to the appended drawings wherein FIG. 1 schematically shows the plasmid pAK492;

FIG. 2 shows part of the DNA sequence encoding the signal peptide/leader/MI3 insulin precursor;

FIG. 3 shows the construction of the plasmid pAK546;

FIG. 4 shows the amino acid sequence of the leader SEQ ID No. 4 and the DNA sequence encoding it;

FIG. 5 shows the DNA sequence of S. cerevisiae expression plasmid pAK546 encoding the YAP3 signal peptide, leader SEQ ID No. 4 and the MI3 insulin precursor and the encoded amino acid sequence;

FIG. 6 shows the amino acid sequence of the leader SEQ 112) No. 6 and the DNA sequence encoding it;

FIG. 7 shows the amino acid sequence of the leader SEQ ID No. 8 and the DNA sequence encoding it;

FIG. 8 shows the amino acid sequence of the leader SEQ ID No. 17 and the DNA sequence encoding it;

FIG. 9 shows the amino acid sequence of the leader SEQ ID No. 16 and the DNA sequence encoding it;

FIG. 10 shows the amino acid sequence of the leader SEQ ID No. 19 and the DNA sequence encoding it;

FIG. 11 shows the amino acid sequence of the leader SEQ ID No. 20 and the DNA sequence encoding it;

FIG. 12 shows the amino acid sequence of the leader SEQ ID No. 21 and the DNA sequence encoding it;

FIG. 13 shows the DNA fragment of pAK527 used as the direct template in the construction of SEQ ID Nos. 4 and 6;

FIG. 14 shows the DNA fragment of pAK531 used as the direct template in the construction of SEQ ID No. 8;

FIG. 15 shows the DNA fragment of pAK555 used as the direct template in the construction of SEQ ID Nos. 16 and 17;

FIG. 16 shows the DNA fragment of pAK559 used as the direct template in the construction of SEQ ID Nos. 19 and 20; and FIG. 17 shows the DNA fragment of pAK562 used as the direct template in the construction of SEQ ID No. 21;

FIG. 18 shows the amino acid sequence of the leader SEQ ID No. 27 and the DNA sequence SEQ ID No. 66 encoding it;

FIG. 19 shows the amino acid sequence SEQ ID No. 71 of an N-terminally extended MI3 insulin precursor and the DNA sequence SEQ ID No. 70 encoding it;

FIG. 20 shows the amino acid sequence of the leader SEQ ID No. 69 and the DNA sequence SEQ ID No. 68 encoding it;

FIG. 21 shows the DNA fragment SEQ ID No. 72 of pAK614 used as the direct template in the construction of SEQ ID No. 27; and FIG. 22 shows the DNA fragment SEQ ID No. 73 of pAK625 used as the direct template in the construction of SEQ ID No. 69.

DETAILED DISCLOSURE OF THE INVENTION

Figure 1:
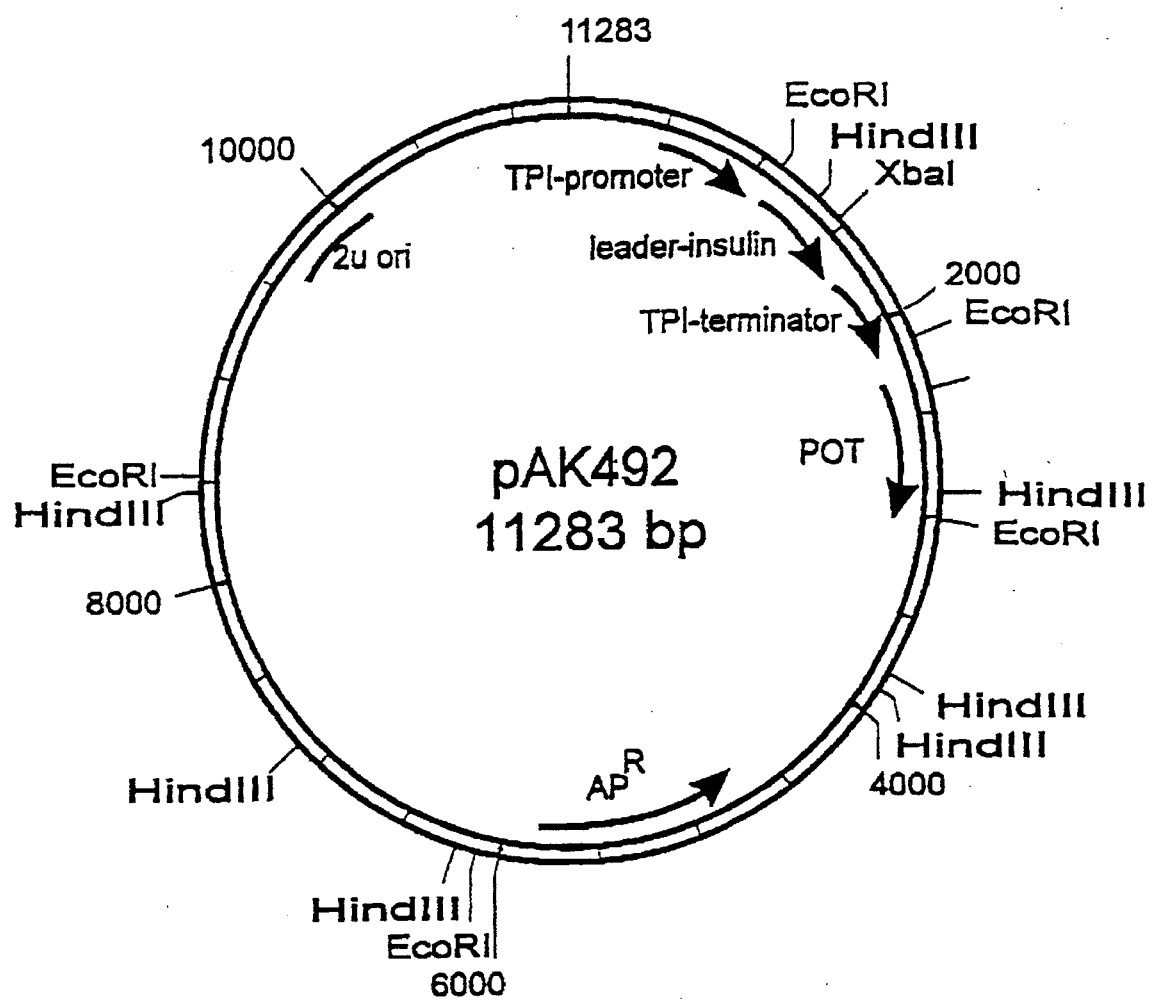

When $X^1$ in general formula I designates an amino acid, it is preferably Ser, Thr or Ala. When $X^2$ in general formula I designates one amino acid, it is preferably Ser, Thr or Ala. When $X^2$ in general formula I designates a sequence of two amino acids, it is preferably SerIle. When $X^2$ in general formula I designates a sequence of three amino acids, it is preferably SerAlaIle. When $X^2$ in general formula I designates a sequence of four amino acids it is preferably SerPheAlaThr (SEQ ID NO: 22). In a preferred embodiment, $X^3$ is an amino acid sequence of the general formula II $$X^4X^5\text{-}X^6 \quad (II)$$

wherein $X^4$ is a sequence of from 1 to 21 codable amino acids which may be the same or different, $X^5$ is Pro or one of the amino acid sequences ValAsnLeu or LeuAlaAsnValAlaMetAla (SEQ ID NO: 26), and $X^6$ is a sequence of from 1 to 8 codable amino acids which may be the same or different.

In general formula II, X4 is preferably an amino acid sequence which includes one or more of the motifs LeuValAsnLeu (SEQ ID NO: 16), SerValAsnLeu (SEQ ID NO: 1), MetAlaAsp, ThrGluSer, ArgPheAlaThr (SEQ ID NO: 23) or ValAlaMetAla (SEQ ID NO: 20); or $X^4$ is an amino acid sequence which includes the sequence AsnSerThr or AsnThrThr; or $X^4$ is an amino acid sequence which includes the sequence
(Ser/Leu)ValAsnLeu (SEQ ID NO: 1 and 16),
(Ser/Leu)ValAsnLeuMetAlaAsp (SEQ ID NOS: 61 and 78), (Ser/Leu)ValAsnLeuMetAlaAspAsp (SEQ ID NOS: 61 and 78),
(Ser/Leu)ValAsnLeuMetAlaAspAspThrGluSer (SEQ ID NOS: 61 and 78),
(Ser/Leu)ValAsnLeuMetAlaAspAspThrGluSerIle (SEQ ID NOS: 61 and 78) or
(Ser/Leu)ValAsnLeuMetAlaAspAspThrGluSerArgPheAlaThr (SEQ ID NO: 73); or $X^4$ is an amino acid sequence which includes the sequence
Asn(Thr/Ser)ThrLeu (SEQ ID NOS: 79 and 80),
Asn(Thr/Ser)ThrLeuAsnLeu (SEQ ID NOS: 81 and 82) or
Asn(Thr/Ser)ThrLeuValAsnLeu (SEQ ID NO: 16); or any combination thereof.

In general formula II, $X^5$ is preferably Pro or an amino acid sequence which includes the sequence ValAsnLeu, LeuAlaAsnValAlaMetAla (SEQ ID NO: 26), LeuAspValValAsnLeuProGly or LeuAspValValAsnLeuIleSerMet (SEQ ID NO: 74) (SEQ ID NO: 83)

When $X^6$, in general formula II, designates one amino acid, it is preferably Ala, Gly, Leu, Thr, Vat or Ser. When $X^6$, in general formula II, designates a sequence of two amino acids, it is preferably GlyAla or SerAla. When $X^6$, in general formula II, designates a sequence of three amino acids, it is preferably AlaValAla. When $X^6$, in general formula II, designates a sequence of eight amino acids, it is preferably GlyAlaAspSerLysThrValGlu (SEQ ID NO: 84).

Examples of preferred leader peptides coded for by the DNA sequence LS are:

| | |
|---|---|
| SEQ ID No. 1 | GlnProIleAspGluAspAsnAspThrSerValAsnLeuProAla; |
| SEQ ID No. 2 | GlnProIleAspAspGluAsnThrThrSerValAsnLeuProAla; |
| SEQ ID No. 3 | GlnProIleAspAspGluSerAsnThrThrSerValAsnLeuProAla; |
| SEQ ID No. 4 | GlnProIleAspAspGLuAsnThrThrSerValAsnLeuProVal; |
| SEQ ID No. 5 | GlnProIleAspAspThrGluAsnThrThrSerValAsnLeuProAla; |
| SEQ ID No. 6 | GlnProIleAspAspThrGlulSerAsnThrThrSerValAsnLeuProAla; |
| SEQ ID No. 7 | GlnProIleAspAspGluAsnThrThrSerValAsnLeuMetAla; |
| SEQ ID No. 8 | GlnProIleAspAspThrGluSerAsnThrThrSerValAsnLeuProGlyAla; |
| SEQ ID No. 9 | GlnProIleAspAspThrGluSerAsnThrThrSerValAsnLeuMetAla; |
| SEQ ID No. 10 | GlnProIleAspAspThrGluSerAsnThrThrSerValAsnValProThr; |
| SEQ ID No. 11 | GlnProIleAspAspThrGluSerAsnThrThrLeuValAsnValProThr; |
| SEQ ID No. 12 | GlnProIleAspAspThrGluSerAsnThrThrSerValAsnLeuProThr; |
| SEQ ID No. 13 | GlnProIleAspAspThrGluSerAsnThrThrLeuValAsnValProGlyAla; |
| SEQ ID No. 14 | GlnProIleAspAspThrGluSerAsnThrThrSerValAsnLeuMetAlaPro-AlaValAla; |
| SEQ ID No. 15 | GlnProIleAspAspThrGluSerAsnThrThrSerValAsnLeuMetAspLeuAla-ValGlyLeuProGlyAla; |
| SEQ ID No. 16 | GlnProIleAspAspThrGluSerAsnThrThrSerValAsnLeuMetAlaAsp-AspThrGluSerIleAsnThrThrLeuValAsnLeuProGlyAla; |
| SEQ ID No. 17 | GlnProIleAspAspThrGluSerIleAsnThrThrLeuValAsnLeuProGlyAla; |
| SEQ ID No. 18 | GlnProIleAspAspThrGluSerAsnThrThrLeuValAsnLeuProGlyAla; |
| SEQ ID No. 19 | GlnProIleAspAspThrGluSerAsnThrThrSerValAsnLeuMet AlaAsp-AspThrGluSerArgPheAlaThrAsnThrThrLeuValAsnLeuProLeu; |
| SEQ ID No. 20 | GlnProIleAspAspThrGluSerAsnThrThrSerValAsnLeuMetAlaAsp-AspThrGluSerIleAsnThrThrLeuValAsnLeuAlaAsnValAlaMetAla; |
| SEQ ID No. 21 | GlnProIleAspAspThrGluSerAlaIleAsnThrThrLeuValAsnLeuProGlyAla; |
| SEQ ID No. 22 | GlnProIleAspAspThrGluSerPheAlaThrAsnThrThrLeuValAsn-LeuProGlyAla; |
| SEQ ID No. 23 | GlnProIleAspAspThrGluSerIleAsnThrThrLeuValAsnLeuMetAlaAsp-AspThrGluSerArgPheAlaThrAsnThrThrLeuValAsnLeuProLeu; |
| SEQ ID No. 24 | GlnProIleAspAspThrGluSerIleAsnThrThrLeuValAsnLeuMetAla-AspAspThrGluSerArgPheAlaThrAsnThrThrLeuAspValValAsn-LeuProGlyAla; |
| SEQ ID No. 25 | GlnProIleAspAspThrGluSerAlaAlaIleAsnThrThrLeuValAsnLeu-ProGlyAla; |
| SEQ ID No. 26 | GlnProIleAspAspThrGluSerAsnThrThrSerValAsnLeuMetAlaAspAsp-ThrGluSerArgPheAlaThrAsnThrThrLeuValAsnLeuAlaAsnVal-AlaMetAla; |
| SEQ ID No. 27 | GlnProIleAspAspThrGluSerAsnThrThrSerValAsnLeuMetAlaAspAsp-ThrGluSerArgPheAlaThrAsnThrThrLeuAspValValAsanLeuIleSerMetAla; |
| SEQ ID No. 28 | GlnProIleAspAspThrGluSerAsnThrThrSerValAsnLeuMetAlaAsn-ThrThrGluSerArgPheAlaThrAsnThrThrLeuAspValValAsnLeuIle-SerMetAla; and |
| SEQ ID No. 69 | GlnProIleAspAspThrGluSerAsnThrThrSerValAsnLeuMet-AlaAspAspThrGluSerArgPheAlaThrAsnThrThrLeuAlaLeu-AspValValAsnLeuIleSerMetAla. |

Particularly preferred leader peptides coded for by the DNA sequence LS are:

| | |
|---|---|
| SEQ ID No. 15 | GlnProIleAspAspThrGluSerAsnThrThrSerValAsnLeuMet-AspLeuAlaValGlyLeuProGlyAla; |
| SEQ ID No. 16 | GlnProIleAspAspThrGluSerAsnThrThrSerValAsnLeuMet-AlaAspAspThrGluSerIleAsnThrThrLeuValAsnLeuProGlyAla; |
| SEQ ID No. 17 | GlnProIleAspAspThrGluSerIleAsnThrThrLeuValAsnLeuProGlyAla; |
| SEQ ID No. 18 | GlnProIleAspAspThrGluSerAsnThrThrLeuValAsnLeuProGlyAla; |

-continued

| SEQ ID No. 19 | GlnProIleAspAspThrGluSerAsnThrThrSerValAsnLeuMet-AlaAspAspThrGluSerArgPheAlaThrAsnThrThrLeuValAsnLeuProLeu; |
|---|---|
| SEQ ID No. 20 | GlnProIleAspAspThrGluSerAsnThrThrSerValAsnLeuMet-AlaAspAspThrGluSerIleAsnThrThrLeuValAsnLeuAlaAsnValAlaMetAla; |
| SEQ ID No. 21 | GlnProIleAspAspThrGluSerAlaIleAsnThrThrLeuValAsnLeuProGlyAla; |
| SEQ ID No. 22 | GlnProIleAspAspThrGluSerPheAlaThrAsnThrThrLeuVal-AsnLeuProGlyAla; |
| SEQ ID No. 23 | GlnProIleAspAspThrGluSerIleAsnThrThrLeuValAsnLeu-MetAlaAspAspThrGluSerArgPheAlaThrAsnThrThrLeuVal-AsnLeuProLeu; |
| SEQ ID No. 24 | IleAsnThrThrLeuValAsnLeu-MetAlaAspAspThrGluSerArgPheAlaThrAsnThrThrLeuAsp-ValValAsnLeuProGlyAla; |
| SEQ ID No. 25 | GlnProIleAspAspThrGluSerAlaAlaIleAsnThrThrLeuVal-AsnLeuProGlyAla; |
| SEQ ID No. 26 | GlnProIleAspAspThrGluSerAsnThrThrSerValAsnLeuMet-AlaAspAspThrGluSerArgPheAlaThrAsnThrThrLeuValAsn-LeuAlaAsnValAlaMetAla; and |
| SEQ ID No. 28 | GlnProIleAspAspThrGluSerAsnThrThrSerValAsnLeuMet-AlaAsnThrThrGluSerArgPheAlaThrAsnThrThrLeuValAspVal-ValAsnLeuIleSerMetAla. |
| SEQ ID No. 69 | GlnProIleAspAspThrGluSerAsnThrThrSerValAsnLeuMet-AlaAspAspThrGluSerArgPheAlaThrAsnThrThrLeuAlaLeu-AspValValAsnLeuIleSerMetAla. |

The signal sequence (SP) may encode any signal peptide which ensures an effective direction of the expressed polypeptide into the secretory pathway of the cell. The signal peptide may be a naturally occurring signal peptide or functional parts thereof or it may be a synthetic peptide. Suitable signal peptides have been found to be the α-factor signal peptide, the signal peptide of mouse salivary amylase, a modified carboxypeptidase signal peptide, the yeast BAR1 signal peptide or the *Humicola lanuginosa* lipase signal peptide or a derivative thereof. The mouse salivary amylase signal sequence is described by Hagenbüchle, O. et at., *Nature* 289 (1981) 643–646. The carboxypeptidase signal sequence is described by Valls, L. A. et al., *Cell* 48 (1987) 887–897. The BAR1 signal peptide is disclosed in WO 87/02670. The yeast aspartic protease 3 signal peptide is described in Danish patent application No. 0828/93.

The yeast processing site encoded by the DNA sequence PS may suitably be any paired combination of Lys and Arg, such as LysArg, ArgLys, ArgArg or LysLys which permits processing of the polypeptide by the KEX2 protease of *Saccharomyces cerevisiae* or the equivalent protease in other yeast species (Julius, D. A. et at., *Cell* 37 (1984) 1075). If KEX2 processing is not convenient, e.g. if it would lead to cleavage of the polypeptide product, e.g. due to the presence of two consecutive basic amino acid internally in the desired product, a processing site for another protease may be selected comprising an amino acid combination which is not found in the polypeptide product, e.g. the processing site for $FX_a$, IleGluGlyArg (SEQ ID NO: 89) (cf. Sambrook, J., Fritsch, E. F. and Maniatis, T., *Molecular Cloning: A Laboratory Manual*, Cold Spring Harbor Laboratory Press, New York, 1989).

The protein produced by the method of the invention may be any protein which may advantageously be produced in yeast. Examples of such proteins are heterologous proteins such as aprotinin, tissue factor pathway inhibitor or other protease inhibitors, insulin or insulin precursors, human or bovine growth hormone, interleukin, glucagon, GLP-1, IGF-I, IGF-II, tissue plasminogen activator, transforming growth factor α or β, platelet-derived growth factor, enzymes or a functional analogue thereof. In the present context, the term "functional analogue" is meant to indicate a protein with a similar function as the native protein (this is intended to be understood as relating to the nature rather than the level of biological activity of the native protein). The protein may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above. Also, precursors or intermediates for other proteins may be produced by the method of the invention. An example of such a precursor is the MI3 insulin precursor which comprises the amino acid sequence B(1–29)AlaAlaLysA(1–21) wherein A(1–21) is the A chain of human insulin and B(1–29) is the B chain of human insulin in which Thr(B30) is missing.

Preferred DNA constructs encoding leader sequences are as shown in FIGS. 4–12 or suitable modifications thereof. Examples of suitable modifications of the DNA sequence are nucleotide substitutions which do not give rise to another amino acid sequence of the protein, but which may correspond to the codon usage of the yeast organism into which the DNA construct is inserted or nucleotide substitutions which do give rise to a different amino acid sequence and therefore, possibly, a different protein structure. Other examples of possible modifications are insertion of one or more codons into the sequence, addition of one or more codons at either end of the sequence and deletion of one or more codons at either end of or within the sequence.

The recombinant expression vector carrying the expression casette

5'-P-SP-LS-PS-*gene*-(T)$_i$-3' wherein P, SP, LS, *gene*, T and i are as defined above may be any vector which is capable of replicating in yeast organisms. The promoter may be any DNA sequence which shows transcriptional activity in yeast and may be derived from genes encoding proteins either homologous or heterologous to yeast. The promoter is preferably derived from a gene encoding a protein homologous to yeast. Examples of suitable promoters are the *Saccharomyces cerevisiae* MFα1, TPI, ADH or PGK promoters.

The sequences shown above should preferably also be operably connected to a suitable terminator, e.g. the TPI terminator (cf. Alber, T. and Kawasaki, G., *J. Mol. Appl. Genet.* 1 (1982) 419–434).

The recombinant expression vector of the invention further comprises a DNA sequence enabling the vector to replicate in yeast. Examples of such sequences are the yeast plasmid 2 μreplication genes PEP 1-3 and origin of replication. The vector may also comprise a selectable marker, e.g. the *Schizosaccharomyces pombe* TPI gene as described by Russell, P. R., *Gene* 40 (1985) 125-130.

The methods used to ligate the sequence 5'-P-SP-LS-PS-*gene*-Cr)$_i$-3' and to insert it into suitable yeast vectors containing the information necessary for yeast replication, are well known to persons skilled in the art (cf., for instance, Sambrook, J., Fritsch, E. F. and Maniatis, T., op.cit.). It will be understood that the vector may be constructed either by first preparing a DNA construct containing the entire sequence 5'-P-SP-LS-PS-*gene*-(T)$_i$-3' and subsequently inserting this fragment into a suitable expression vector, or by sequentially inserting DNA fragments into a suitable vector containing genetic information for the individual elements (such as the promoter sequence, the signal peptide, the leader sequence GlnProIle(Asp/Glu)(Asp/Glu)X$^1$(Gh/Asp)X$^2$AsnZ(Thr/Ser)X$^3$ (SEQ ID NO: 77), the processing site, the polypeptide, and, if present, the terminator sequence) followed by ligation.

The yeast organism used in the method of the invention may be any suitable yeast organism which, on cultivation, produces large amounts of the desired polypeptide. Examples of suitable yeast organisms may be strains of the yeast species *Saccharomyces cerevisiae*, *Saccharomyces kluyveri*, *Schizosaccharomyces pombe* or *Saccharomyces uvarum*. The transformation of the yeast cells may for instance be effected by protoplast formation followed by transformation in a manner known per se. The medium used to cultivate the cells may be any conventional medium suitable for growing yeast organisms. The secreted polypeptide, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography or the like.

The invention is further described in the following examples which are not to be construed as limiting the scope of the invention as claimed.

EXAMPLES

Plasmids and DNA Material

All expression plasmids are of the C-POT type. Such plasmids are described in EP patent application No. 171 142 and are characterized in containing the *Schizosaccharomyces pombe* triose phosphate isomerase gene (POT) for the purpose of plasmid selection and stabilization. A plasmid containing the POT-gene is available from a deposited *E. coli* strain (ATCC 39685). The plasmids furthermore contain the *S. cerevisiae* triose phosphate isomerase promoter and terminator (P$_{TPI}$ and T$_{TPI}$). They are identical to pMT742 (Egel-Mitani, M. et al., *Gene* 73 (1988) 113–120) (see FIG. 1) except for the region defined by the EcoR I-Xba I restriction sites encompassing the coding region for signal/leader/product.

The plasmids pAK527, pAK531, pAK555, pAK559, pAK562, pAK614 and pAK625 were used as DNA templates in the PCR reactions applied in the construction of the leaders described in the examples. The synthetic DNA fragments serving as the direct template are shown in FIGS. 13–17. With the exception of the shown DNA regions the plasmids are identical to pAK492 shown in FIG. 1.

Synthetic DNA fragments were synthesized on an automatic DNA synthesizer (Applied Biosystems model 380A) using phosphoramidite chemistry and commercially available reagents (Beaucage, S. L. and Caruthers, M. H., *Tetrahedron Letters* 22 (1981) 1859–1869).

All other methods and materials used are common state of the art knowledge (see, e.g. Sambrook, J., Fritsch, E. F. and Maniatis, T., *Molecular Cloning: A Laboratory Manual*, Cold Spring Harbor Laboratory Press, New York, 1989).

EXAMPLE 1

Synthesis of the leader SEQ ID No. 4 for expression of the MI3 insulin precursor in *S. cerevisiae* (strain yAK546).

The leader SEQ ID No. 4 has the following amino acid sequence: GlnProIleAspAspGlu-AsnThrThrSerValAsnLeuProVal The following oligonucleotides were synthesised:

94 5'-TAAATCTATAACTACAAAAAACACATA-3' SEQ ID No. 29

333 5'-GACTCTCTTAACTGGCAAGTTGACA-3' SEQ ID No. 30

312 5'-AAGTACAAAGCTTCAACCAAGTGAGAAC-CACACAAGTGTT GGTTAACGAATCTCTT-3' SEQ ID No. 31

1845 5'-CATACACAATATAAACGACGG-3' SEQ ID No. 32

The following polymerase chain reactions (PCR) were performed using the Gene Amp PCR reagent kit (Perkin Elmer, 761 Main Avewalk, Conn. 06859, USA) according to the manufacturers instructions. During the reaction, the PCR mixtures were overlayed with 100 μl of mineral oil (Sigma Chemical CO, St. Louis Mo., USA):

Polymerase Chain Reaction No. 1

5 μl of oligonucleotide #94 (50 pmol)
5 μl of oligonucleotide #333 (50 pmol)
10 μl of 10X PCR buffer
16 μl of dNTP mix
0.5 μl of Taq enzyme
0.5 μl of pAK527 plasmid (FIG. 13) as template (0.2 μg of DNA)
63 μl of water A total of 12 cycles were performed, one cycle was 94° C. for 1 min; 37° C. for 2 min; 72° C. for 3 min. The PCR mixture was then loaded onto a 2% agarose gel and electrophoresis was performed using standard techniques (Sambrook, J., Fritsch, E. F. and Maniatis, T., op.cit.). The resulting DNA fragment was cut out of the agarose gel and isolated using the Gene Clean kit (Bio 101 inc., PO BOX 2284, La Jolla, Calif. 92038, USA) according to the manufacturers instructions.

Polymerase Chain Reaction No. 2

5 μl of oligonucleotide #312 (50 pmol)
5 μl of oligonucleotide #94 (50 pmol)
10 μl of 10X PCR buffer
16 μl of dNTP mix
0.5 μl of Taq enzyme
10 μl of purified DNA fragment from PCR No. 1
53.5 μl of water A total of 12 cycles were performed, one cycle was 94° C. for 1 min; 37° C. for 2 min; 72° C. for 3 min.

The DNA fragment from polymerase chain reaction No. 2 was isolated and purified using the Gene Clean kit (Bio 101 inc., PO BOX 2284, La Jolla, Calif. 92038, USA) according to the manufacturers instructions.

The purified PCR DNA fragment was dissolved in 10 μl of water and restriction endonuclease buffer and cut with the restriction endonucleases Asp 718 and Hind III in a total volume of 15 μl according to standard techniques (Sambrook, J., Fritsch, E. F. and Maniatis, T., op.cit.). The 167 bp Asp 718/Hind III DNA fragment was subjected to electrophoresis on agarose gel and purified using The Gene Clean Kit as described.

The S. cerevisiae expression plasmid pAK492 (shown in FIG. 1) is a derivative of the previously described plasmid pMT742 in which the fragment encoding the signal/leader/insulin precursor has been replaced by the EcoR I-Xba I fragment shown in FIG. 2. This fragment has been synthesized on an Applied Biosystems DNA synthesizer in accordance with the manufacturer's instructions. The plasmid pAK492 was cut with the restriction endonucleases Asp 718 and Xba I and the vector fragment of 10986 bp was isolated. The plasmid pAK492 was cut with the restriction endonucleases Hind III and Xba I and the DNA fragment of 140 bp encoding part of the MI3 insulin precursor was isolated. The three DNA fragments were ligated together using T4 DNA ligase under standard conditions (Sambrook, J., Fritsch, E. F. and Maniatis, T., op.cit.). The ligation mixture was then transformed into a competent E. coli strain (R−, M+) and transformants were identified by ampicillin resistance. Plasmids were isolated from the resulting E. coli colonies using standard DNA miniprep technique (Sambrook, J., Fritsch, E. F. and Maniatis, T., op.cit.), checked with appropriate restrictions endonucleases i.e. EcoR I, Xba I, Nco I and Hind III. The selected plasmid, pAK546, was shown by DNA sequencing analysis (Sequenase, U.S. Biochemical Corp.) using the primer #94 to contain a DNA sequence encoding the leader SEQ ID No. 4. For the DNA sequence encoding the leader SEQ ID No. 4, see FIG. 4). The plasmid pAK546 was transformed into S. cerevisiae strain MT663 as described in European published patent application No. 214 826 and the resulting strain was named yAK546. The DNA sequence of the protein coding region of the expression plasmid is given in FIG. 5.

EXAMPLE 2

Synthesis of the leader SEQ ID No. 6 for expression of the MI3 insulin precursor in S. cerevisiae (strain yAK531).

The leader SEQ ID No. 6 has the following amino acid sequence: GlnProIleAspAspThr-GluSerAsnThrThrSerValAsnLeuProAla The following oligonucleotide was synthesised:
331 5'-GAATCTCTTAGCTGGCAAGTTGACAGAAG-TAGTGTTAGTTTCAGAGTCGTCAATT-3' SEQ ID No. 33

The polymerase chain reaction was performed as described in Example 1 with the expection that oligonucleotide #331 was used instead of oligonucleotide #333.

The Asp 718/Hind III DNA fragment of 168 bp was subjected to electrophoresis on agarose gel and purified as described in Example 1. The Asp 7 18/Hind III DNA fragment was subcloned into the S. cerevisiae expression plasmid as described in Example 1. The selected plasmid, pAK531, was shown by DNA sequencing analysis, as described in Example 1, to contain a DNA sequence encoding the leader SEQ ID No. 6. For the DNA sequence encoding the leader SEQ ID No. 6, see FIG. 6. The plasmid pAK531 was transformed into S. cerevisiae strain MT663 as described in European patent application 86306721.1 and the resulting strain was named yAK531. The DNA sequences encoding the signal peptide and the insulin precursor MI3 were the same as those shown in FIG. 5.

EXAMPLE 3

Synthesis of the leader SEQ ID No. 8 for expression of the MI3 insulin precursor in S. cerevisiae (strain yAK547).

The leader SEQ ID No. 8 has the following amino acid sequence:
GlnProIleAspAspThr-GluSerAsnThrThrSerValAsnLeuProGlyAla The following oligonucleotide was synthesised:
345 5'-AACGAATCTCTTAGCACCT-GGCAAGTTGACAGAAGT-3' SEQ ID No. 34

The polymerase chain reaction was performed as described in Example 1 with the expection that oligonucleotide #345 was used instead of oligonucleotide #333 and plasmid pAK531 (FIG. 14) was used as template.

The Asp 718/Hind III DNA fragment of 171 bp was subjected to electrophoresis on agarose gel and purified as described in Example 1. The Asp 718/Hind III DNA fragment was subcloned into the S. cerevisiae expression plasmid as described in Example 1. The selected plasmid, pAK547, was shown by DNA sequencing analysis, as described in Example 1, to contain a DNA sequence encoding the leader SEQ ID No. 8. For the DNA sequence encoding the leader SEQ ID No. 8, see FIG. 7. The plasmid pAK547 was transformed into S. cerevisiae strain MT663 as described in European patent application No. 86306721.1 and the resulting strain was named yAK547. The DNA sequences encoding the signal peptide and the insulin precursor MI3 were the same as those shown in FIG. 5.

EXAMPLE 4

Synthesis of the leader SEQ ID No. 17 for expression of the MI3 insulin precursor in S. cerevisiae (strain yAK561).

The leader SEQ ID No. 17 has the following amino acid sequence: GlnProIleAspAspThrGluSe-rIleAsnThrThrLeuValAsnLeuProGlyAla The following oligonucleotide was synthesised:
376 5'-AACGAATCTCTTAGCACCTGGCAAGTF-GACCAAAGTAG
TGTTGATAGATTCAGTGTCGTC-3' SEQ ID No. 35

The polymerase chain reaction was performed as described in Example 1 with the expection that oligonucleotide #376 was used instead of oligonucleotide #333 and plasmid pAK555 (FIG. 15) was used as template.

The Asp 718/Hind III DNA fragment of 180 bp was subjected to electrophoresis on agarose gel and purified as described in Example 1. The Asp 718/Hind III DNA fragment was subcloned into the S. cerevisiae expression plasmid as described in Example 1. The selected plasmid, pAK561, was shown by DNA sequencing analysis, as described in Example 1, to contain a DNA sequence encoding the leader SEQ ID No. 17. For the DNA sequence encoding the leader SEQ ID No. 17, see FIG. 8. The plasmid pAK561 was transformed into S. cerevisiae strain MT663 as described in European patent application No. 86306721.1 and the resulting strain was named yAK561. The DNA sequences encoding the signal peptide and the insulin precursor MI3 were the same as those shown in FIG. 5.

EXAMPLE 5

Synthesis of the leader SEQ ID No. 16 for expression of the MI3 insulin precursor in S. cerevisiae (strain yAK559).

The leader SEQ ID No. 16 has the following amino acid sequence:

GlnProIleAspAspThr-GluSerAsnThrThrSerValAsnLeu-MetAlaAspAspThrGluSe-rIleAsnThrThrLeuValAsnLeuProGlyAla The following oligonucleotide was synthesised:

375 5'-AACGAATCTCTTA GCACCTGGCAAGT-TAACCAAAGTAGTGTTGATAGATTCAGT-GTCGTCAGCCATCAAGTTrGAC-3' SEQ ID No. 36

The polymerase chain reaction was performed as described in Example 1 with the expection that oligonucleotide #375 was used instead of oligonucleotide #333 and plasmid pAK555 (FIG. 15) was used as template.

The Asp 718/Hind III DNA fragment of 222 bp was subjected to electrophoresis on agarose gel and purified as described in Example 1. The Asp 718/Hind III DNA fragment was subcloned into the *S. cerevisiae* expression plasmid as described in Example 1. The selected plasmid, pAK559, was shown by DNA sequencing analysis, as described in Example 1, to contain a DNA sequence encoding the leader SEQ ID No. 16. For the DNA sequence encoding the leader SEQ ID No. 16, see FIG. 9. The plasmid pAK559 was transformed into *S. cerevisiae* strain MT663 as described in European patent application No. 86306721.1 and the resulting strain was named yAK559. The DNA sequences encoding the signal peptide and the insulin precursor MI3 were the same as those shown in FIG. 5.

EXAMPLE 6

Synthesis of the leader SEQ ID No. 19 for expression of the MI3 insulin precursor in *S. cerevisiae* (strain yAK580).

The leader SEQ ID No. 19 has the following amino acid sequence:

GlnProIleAspAspThrGluSerAsnThrThrSerValAsnLeu MetAlaAspAspThrGluSerArg-PheAlaThrAsnThrThrLeuValAsnLeuProLeu

The following oligonucleotide was synthesised:

384 5'-AACGAATCTCTTCAATGGCAAGTYAAC-CAAAGTAGTGT TAGTAGCGAATCTAGATTCAGTGTCGTCAGCCAT-3' SEQ ID No. 37

The polymerase chain reaction was performed as described in Example 1 with the expection that oligonucleotide #384 was used instead of oligonucleotide #333 and plasmid pAK559 (FIG. 16) was used as template.

The Asp 718/Hind 1211 DNA fragment of 228 bp was subjected to electrophoresis on agarose gel and purified as described in Example 1. The Asp 718/Hind III DNA fragment was subcloned into the *S. cerevisiae* expression plasmid as described in Example 1. The selected plasmid, pAK580, was shown by DNA sequencing analysis, as described in Example 1, to contain a DNA sequence encoding the leader SEQ ID No. 19. For the DNA sequence encoding the leader SEQ ID No. 19, see FIG. 10. The plasmid pAK580 was transformed into *S. cerevisiae* strain MT663 as described in European patent application No. 86306721.1 and the resulting strain was named yAK580. The DNA sequences encoding the signal peptide and the insulin precursor MI3 were the same as those shown in FIG. 5.

EXAMPLE 7

Synthesis of the leader SEQ ID No. 20 for expression of the MI3 insulin precursor in *S. cerevisiae* (strain yAK583).

The leader SEQ ID No. 20 has the following amino acid sequence:

GlnProIleAspAspThrGluSerAsn ThrThrSerValAsnLeu-MetAlaAspAspThrGluSe-rIleAsnThrThrLeuValAsnLeuAlaAsnValAlaMetAla

The following oligonucleotide was synthesised:

390 5'-AACGAATCTCTTAGCCATGGCAACGT-TAGCCAAGTTAA CCAAAGT-3' SEQ ID No. 38

The polymerase chain reaction was performed as described in Example 1 with the expection that oligonucleotide #390 was used instead of oligonucleotide #333 and plasmid pAK559 (FIG. 16) was used as template.

The Asp 718/Hind III DNA fragment of 231 bp was subjected to electrophoresis on agarose gel and purified as described in Example 1. The Asp 718/Hind III DNA fragment was subcloned into the *S. cerevisiae* expression plasmid as described in Example 1. The selected plasmid, pAK583, was shown by DNA sequencing analysis, as described in Example 1, to contain a DNA sequence encoding the leader SEQ ID No. 20. For the DNA sequence encoding the leader SEQ ID No. 20, see FIG. 11. The plasmid pAK583 was transformed into *S. cerevisiae* strain MT663 as described in European patent application No. 86306721.1 and the resulting strain was named yAK583. The DNA sequences encoding the signal peptide and the insulin precursor MI3 were the same as those shown in FIG. 5.

EXAMPLE 8

Synthesis of the leader SEQ ID No. 21 for expression of the MI3 insulin precursor in *S. cerevisiae* (strain yAK586).

The leader SEQ ID No. 21 has the following amino acid sequence:

GlnProIleAspAspThrGluSer-AlaIleAsnThrThrLeuValAsnLeuProGlyAla

The following oligonucleotide was synthesised:

401 5'-AACGAATCTCTTAGCACCTGGCAAGTTGAC-CAAAGTAG TGTTGATAGCAGATTCAGTGTCG-3' SEQ ID No. 39

The polymerase chain reaction was performed as described in Example 1 with the exception that oligonucleotide #401 was used instead of oligonucleotide #333 and plasmid pAK562 (FIG. 17) was used as template.

The Asp 718/Hind III DNA fragment of 183 bp was subjected to electrophoresis on agarose gel and purified as described in Example 1. The Asp 718/Hind III DNA fragment was subcloned into the *S. cerevisiae* expression plasmid as described in Example 1. The selected plasmid, pAK586, was shown by DNA sequencing analysis, as described in Example 1, to contain a DNA sequence encoding the leader SEQ ID No. 21, see FIG. 12. The plasmid pAK586 was transformed into *S. cerevisiae* strain MT663 as described in European patent application No. 86306721.1 and the resulting strain was named yAK586. The DNA sequences encoding the signal peptide and the insulin precursor MI3 were the same as those shown in FIG. 5.

EXAMPLE 9

Expression of the MI3 insulin precursor using selected leader sequences according to the present invention.

Yeast strains harbouring plasmids as described above, were grown in YPD medium (Sherman, F. et al., *Methods in Yeast Genetics*, Cold Spring Harbor Laboratory Press, 1981). For each strain 6 individual 5 ml cultures were shaken at 30° C. for 72 hours, with a final $OD_{600}$ of approx.

15. After centrifugation the supenatant was removed for HPLC analysis by which method the concentration of secreted instalin precursor was measured by a method described by Snel, L. et al. *Chromatographia* 24 (1987) 329–332.

In Table 1 the expression levels of the insulin precursor, MI3, obtained by use of selected leader sequences according to the present invention, are given as a percentage of the level obtained with transformants of pMT742, utilizing the MFα(1) leader of *S. cerevisiae*.

TABLE 1

| Leader | Expression level, % |
| --- | --- |
| MT748 α-leader | 100 |
| SEQ ID No. 15 | 87 |
| SEQ ID No. 16 | 215 |
| SEQ ID No. 17 | 157 |
| SEQ ID No. 19 | 166 |
| SEQ ID No. 20 | 86 |
| SEQ ID No. 21 | 145 |
| SEQ ID No. 22 | 137 |
| SEQ ID No. 23 | 121 |

EXAMPLE 10

Synthesis of the leader SEQ ID No. 27 for expression of the extended MI3 insulin precursor in *S. cerevisiae* (strain yAK677).

The leader SEQ ID No. 27 has the following amino acid sequence:

GlnProIleAspAspThrGluSerAsnThrThrSerValAsnLeu
MetAlaAspAspThrGluSerArg-
PheAlaThrAsnThrThrLeuAspValValAsnLeuIleSerMetAla

The following oligonucleotides were synthesised:
440 5'-GGTTAACGAACTTTGGAGCTTCAGCT-
TCAGCITCTTCTCTCTFAGCCAT
GGAGATCAAGTFAACAACATCCAAAGTAGTGTT-3'
(SEQ ID NO: 64) and
441 5'-CAAGTACAAAGCTTCAACCAAGTGGGAAC-
CGCACAAGTGTTGGTTAACG AACTT-3' (SEQ ID NO: 65)

Polymerase chain reactions were performed as described in Example in 1 with the exception that oligonucleotide #440 was used instead of oligonucleotide #333 and plasmid pAK614 was used as template. For the second polymerase chain reaction, oligonucleotide # was used instead of oligonucleotide #312.

The purified PCR DNA fragment was isolated and digested with the restriction endonucleases Asp 718 and Hind III as described in Example 1. The Asp 718/Hind III DNA fragment of 268 bp was subjected to electrophoresis on agarose gel and purified as described in Example 1. The Asp 718/Hind III DNA fragment was subcloned into the *S. cerevisiae* expression plasmid as described in Example 1, with the exception that the 140 bp Hind III/Xba I DNA fragment was derived from pAK602 and encodes Asp$^{B28}$ human insulin. The selected plasmid, pAK616, was shown by DNA sequencing analysis, as described in Example 1, to contain the DNA sequence encoding the leader SEQ ID No. 27. For the DNA sequence, SEQ ID No. 66, encoding the leader SEQ ID No. 27, see FIG. 18. The Asp 718/Hind III DNA fragment of 268 bp from pAK616 was isolated and ligated with the 10986 bp Asp 718/Xba I DNA fragment from pAK601 and the 140 bp DNA fragment Hind III/Xba I from pAK464 (encoding an extended version of Asp$^{B28}$ human insulin) and named pAK 625. The 180 bp Asp 718/Nco I DNA fragment from pAK625 was isolated and ligated with the 221 bp Nco I/Xba I DNA fragment from pJB146 (encoding and extended version of the insulin precursor) and the 10824 bp Asp 718/Xba I DNA fragment from pAK601 and the resulting plasmid was named pAK677. The plasmid pAK677 was transformed into *S. cerevisiae* strain MT663 as described in European patent application 86306721.1 and the resulting strain was named yAK677. With the exception of the DNA sequence encoding the leader, the DNA sequence encoding the signal peptide is as described in FIG. 5. The DNA sequence coding for the extended MI3 insulin precursor is as described in FIG. 19.

EXAMPLE 11

Synthesis of the leader SEQ ID No. 69 for expression of the extended MI3 insulin precursor in *S. cerevisiae* (yAK680)

The leader SEQ ID No. 69 has the following amino acid sequence:
GlnProIleAspAspThr-
GluSerAsnThrThrSerValAsnLeuMetAlaAspAspThr
GluSerArgPheAlaThrAsnThrThr-
LeuAlaLeuAspValValAsnLeuIleSerMet Ala The following oligonucleotide was synthesised:
577 5'-TCTCTTAGCCATGGAGATCAAGTT-
AACAACATCCAAAGCCAAAGTAGTGTF-3' (SEQ ID NO: 67)

The PCR was performed as described in Example in 1 with the exception that oligonucleotide #577 was used instead of oligonucleotide #333 and plasmid pAK625 was used as template and the second PCR was not performed. The PCR fragment was digested with the restriction endonucleases Asp 718 and Nco I as described in Example 1.

The Asp 718/Nco I DNA fragment of 190 bp was subjected to electrophoresis on agarose gel and purified as described in Example 1 expect that the 10824 bp Asp 718/Xba I vector DNA fragment was isolated from and from pAK601. The 190 bp Asp 718/Nco I DNA fragment was subcloned into the *S. cerevisiae* expression plasmid as described in Example 1, expect that the 221 bp DNA fragment Nco I/Xba I (encoding an extended version of the MI3 insulin precursor) was isolated from pAK677 and used instead of the Hind III/Xba I DNA fragment. The selected plasmid was shown by DNA sequencing analysis as described in Example 1 to contain the DNA sequence encoding the leader SEQ ID No. 69 and named pAK680. For the DNA sequence, SEQ ID No. 68, encoding the leader SEQ ID No. 69, see FIG. 20. The plasmid pAK680 was transformed into *S. cerevisiae* strain MT663 as described in European patent application 86306721.1 and the resulting strain was named yAK680. With the exception of the DNA sequence encoding the leader, the DNA sequence encoding the signal peptide is as described in FIG. 5 and the extended insulin precursor MI3 DNA sequence is as described in FIG. 19.

EXAMPLE 12

Expression of N-terminally extended MI3 insulin precursors using the leader sequences SEQ ID No. 27 and SEQ ID No. 69 according to the present invention.

Yeast strains harbouring plasmids as described above, were grown in YPD medium (Sherman, F. et at., *Methods in Yeast Genetics*, Cold Spring Harbor Laboratory Press, 1981). For each strain 6 individual 5 ml cultures were sheen at 30° C. for 72 hours, with a final OD$_{600}$ of approximately 15. After centrifugation the supenatant was removed for HPLC analysis by which method the concentration of secreted insulin precursor was measured by a method described by Snel, L. et at. *Chromatographia* 24 (1987) 329–332.

In Table 2 the expression levels of some N-terminally extended MI3 insulin precursors, obtained by use of the leader sequences SEQ ID No. 27 and SEQ ID No. 69 according to the present invention, are given as a percentage of the level obtained with transformants of pMT742, utilizing the MFα(1) leader of *S. cerevisiae*.

TABLE 2

| Strain | Signal peptide | Leader | Extension | Relative to MT748 |
|---|---|---|---|---|
| MT748 | α | α | | |
| yAK675 | YAP3 | SEQ ID No. 27 | EEAEAEAPK (SEQ ID NO: 85) | 251% |
| yAK677 | YAP3 | SEQ ID No. 27 | EEAEAEAEPK (SEQ ID NO: 86) | 224% |
| yAK681 | YAP3 | SEQ ID No. 69 | EEAEAEAPK (SEQ ID NO: 87) | 248% |
| yAK680 | YAP3 | SEQ ID No. 69 | EEAEAEAEPK (SEQ ID NO: 88) | 362% |

We claim:
1. A DNA expression cassette comprising the following sequence:

5'-P-SP-LS-PS-*gene*-(T)$_r$-3' wherein
(a) P is a promoter sequence,
(b) SP is a DNA sequence encoding a signal peptide,
(c) LS is a DNA sequence encoding a leader peptide selected from the group consisting of:
(i) GlnProIleAspAspThrGluSerAsnThrThrSerValAsnLeuMetAlaAspAspThrGluSerIleAsn ThrThrLeuValAsnLeuProGlyAla (SEQ ID NO: 16);
(ii) GlnProIleAspAspThrGluSerIleAsnThrThrLeuValAsnLeuProGlyAla (SEQ ID No: 17);
(iii) GlnProIleAspAspThrGluSerAsnThrThrSerValAsnLeuMetAlaAsPAsPThrGluSerArgPhe AlaThrAsnThrThrLeuValAsnLeuProLeu (SEQ ID No. 19);
(iv) GlnProIleAspAspThrGluSerAsnThrThrSerValAsnLeuMetAlaAsPAsPThrGluSefIleAsn ThrThrLeuValAsnLeuAlaAsnValAlaMetAla (SEQ ID No:20);
(v) GlnProIleAspAspThrGluSerIleAsnThrThrLeuValAsnLeuMetAlaAsPAsPThrGluSerArg PheAlaThrAsnThrThrLeuValAsnLeuProLeu (SEQ ID No:23);
(vi) GlnProIleAspAspThrGluSerIleAsnThrThrLeuValAsnLeuMetAlaAsPAsPThrGluSerArg PheAlaThrAsnThrThrLeuAspValValAsnLeuProGlyAla (SEQ ID No:24);
(vii) GlnProIleAspAspThrGluSerAlaAlaIleAsnThrThrLeuValAsnLeuProGlyAla (SEQ ID No:25);
(viii) GlnProIleAspAspThrGluSerAsnThrThrSerValAsnLeuMetAlaAspAspThrGluSerArgPhe AlaThrAsnThrThrLeuValAsnLeuAlaAsnValAlaMetAla (SEQ ID No:26);
(ix) GlnProIleAspAspThrGluSerAsnThrThrSerValAsnLeuMetAlaAspAspThrGluSerArgPhe AlaThrAsnThrThrLeuAspValValAsnLeuIleSerMetAla (SEQ ID No:27); and
(x) GlnProIleAspAspThrGluSerAsnThrThrSerValAsnLeuMetAlaAspAspThrGluSerArgPhe AlaThrAsnThrThrLeuAlaLeuAspValValAsnLeuIle SerMetAla[LysArg (SEQ ID No:67)] (SEQ ID No:69);

(e) PS is a DNA sequence encoding a processing site;
(f) *gene* is a DNA sequence encoding a polypeptide;
(g) T is a terminator sequence; and
(h) i is 0 or 1.

2. An expression cassette according to claim 1, wherein LS is GlnProIleAspAspThrOluSerAsnTbxThrSerValAsnLeuMetAlaAspAspThrGluSerIleAsnThr ThrLeuValAsnLeuProGlyAla (SEQ ID NO: 16).

3. An expression cassette according to claim 1, wherein LS is GlnProIleAspAspThrGluSerIleAsnThrThrLcuValAsnLeuProGlyAla (SEQ ID No: 17).

4. An expression cassette according to claim 1, wherein LS is GlnProIleAspAspThrGluScrAsnThrThrSerYalAsnLeuMetAlaAspAspThrGluSerArgPheAla ThrAsnThrThrLeuValAsnLeuProLeu (SEQ ID No. 19).

5. An expression cassette according to claim 1, wherein LS is GlnProIleAspAspThrGluSerAsnThrThrSerValAsnLeuMetAlaAspAAspThrGluSerIleAsnThr ThrLeuValAsnLeuAlaAsnValAlaMetAla (SEQ ID No:20).

6. An expression cassette according to claim 1, wherein LS is GlnProIleAspAspThrGluSerIleAsnThrThrLeuValAsnLeuMetAlaAspAspThrGluSerArgPhe AlaThrAsnThrThrLeuValAsnLeuProLeu (SEQ ID No:23).

7. An expression cassette according to claim 1, wherein LS is GlnProIleAspAspThrGluSerIleAsnThrThrLeuValAsnLeuMetAlaAspAspThrGluSerArgPhe AlaThrAsnThrThrLeuAspValValAsnLeuProGlyAla (SEQ ID No:24).

8. An expression cassette according to claim 1, wherein LS is GlnProIleAspAspThrGluSerAlaAlaIleAsnThrThrLeuValAsnLcuProGlyAla (SEQ ID No:25).

9. An expression cassette according to claim 1, wherein LS is GlnProIleAspAspThrGluSerAsnThrThrSerValAsnLeuMetAlaAspAspThrGhgerAxgPheAla ThrAsnThrThrLeuValAsnLeuAlaAsnValAlaMetAla (SEQ ID No:26).

10. An expression cassette according to claim 1, wherein LS is GlnProIleAspAspThrGluSerAsnThrThrSerValAsnLemMetAlaAspAspThrGluSerArgPheAla ThrAsnThrThrLcuAspValValAsnLeuIleSerMetAla (SEQ ID No:27).

11. An expression cassette according to claim 1, wherein LS is GlnProIleAspAspThrGluSerAsnThrThrSerValAsnLeuMetAlaAspAspThrGluSerArgPheAla ThrAsnThrThrLeuAlaLeuAspValValAsnLeuIleSerMetAla [LysArg (SEQ ID No:67)] (SEQ ID No:69).

12. An expression cassette according to claim 1, wherein the signal peptide is the α-factor signal peptide, the signal peptide of mouse salivary amylase, the carboxypeptidase signal peptide, the yeast aspartic protease 3 signal peptide or the yeast BAR1 signal peptide.

13. An expression cassette according to claim 1, wherein the processing site is LysArg, ArgLys, ArgArg, LysLys or IleGluGlyArg (SEQ ID NO: 89).

14. An expression cassette according to claim 1, wherein the polypeptide is selected from the group consisting of aprotinin, tissue factor pathway inhibitor, or other protease inhibitors, insulin or insulin precursors, insulin-like growth factor I, insulin-like growth factor II, human or bovine growth hormone, interleukin, glucagon, glucagon-like peptide 1, tissue plasminogen activator, transforming growth factor α or β, platelet-derived growth factor, enzymes, and a functional analogue thereof.

15. An expression vector comprising an expression cassette according to claim 1.

16. A yeast cell which is transformed with an expression vector according to claim 15.

17. A process for producing a polypeptide, comprising
(a) culturing the yeast cell of claim 16 in a suitable medium to obtain expression and secretion of the polypeptide; and
(b) recovering the polypeptide from the medium.

\* \* \* \* \*